United States Patent
Cai et al.

(10) Patent No.: US 12,371,753 B2
(45) Date of Patent: Jul. 29, 2025

(54) CO-SOLVENT TO PRODUCE REACTIVE INTERMEDIATES FROM BIOMASS

(71) Applicant: The Regents of the University of California, Oakland, CA (US)

(72) Inventors: Charles M. Cai, Riverside, CA (US); Charles E. Wyman, Riverside, CA (US); Taiying Zhang, Riverside, CA (US); Rajeev Kumar, Riverside, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1042 days.

(21) Appl. No.: 17/008,180

(22) Filed: Aug. 31, 2020

(65) Prior Publication Data
US 2020/0399722 A1 Dec. 24, 2020

Related U.S. Application Data

(63) Continuation of application No. 14/787,090, filed as application No. PCT/US2014/035506 on Apr. 25, 2014, now Pat. No. 10,774,394.

(Continued)

(51) Int. Cl.
*C13K 1/02* (2006.01)
*C07D 307/08* (2006.01)
(Continued)

(52) U.S. Cl.
CPC .............. *C13K 1/02* (2013.01); *C07D 307/08* (2013.01); *C07D 307/50* (2013.01); *C07G 1/00* (2013.01);
(Continued)

(58) Field of Classification Search
CPC .................................................. C12P 2201/00
See application file for complete search history.

(56) References Cited

U.S. PATENT DOCUMENTS

| | | | |
|---|---|---|---|
| 4,058,411 A | 11/1977 | Bellamy et al. | |
| 4,409,032 A | 10/1983 | Paszner et al. | |

(Continued)

FOREIGN PATENT DOCUMENTS

| | | |
|---|---|---|
| EP | 2489780 A1 | 8/2012 |
| WO | 2008/134037 A1 | 11/2008 |

(Continued)

OTHER PUBLICATIONS

Kumar et al. (Biotechnology and Bioengineering, vol. 102 No. 2, 2009, p. 457-467) (Year: 2009).*

(Continued)

*Primary Examiner* — Liam J Heincer
(74) *Attorney, Agent, or Firm* — Buchanan Ingersoll & Rooney PC

(57) ABSTRACT

The disclosure provides a system for production of reactive intermediates from lignocellulosic biomass. The reactive intermediates can be used as platform chemicals for biological conversions or can be further catalytically upgraded to be used as "drop in" reagents for fuels. The disclosure provides methods and compositions useful for processing biomass to biofuels and intermediates.

30 Claims, 18 Drawing Sheets

Related U.S. Application Data

(60) Provisional application No. 61/816,713, filed on Apr. 27, 2013.

(51) Int. Cl.
| | | |
|---|---|---|
| *C07D 307/50* | (2006.01) | |
| *C07G 1/00* | (2011.01) | |
| *C12P 7/10* | (2006.01) | |
| *C12P 17/04* | (2006.01) | |
| *C12P 19/02* | (2006.01) | |
| *D21C 3/20* | (2006.01) | |
| *D21C 3/22* | (2006.01) | |

(52) U.S. Cl.
CPC .............. *C12P 7/10* (2013.01); *C12P 17/04* (2013.01); *C12P 19/02* (2013.01); *D21C 3/20* (2013.01); *D21C 3/222* (2013.01); *C12P 2201/00* (2013.01); *Y02E 50/10* (2013.01)

(56) References Cited

U.S. PATENT DOCUMENTS

| | | | |
|---|---|---|---|
| 4,664,717 A | 5/1987 | Young | |
| 4,806,285 A | 2/1989 | Hoffman et al. | |
| 4,806,474 A | 2/1989 | Hershberger | |
| 5,730,837 A | 3/1998 | Black et al. | |
| 6,479,677 B1* | 11/2002 | Ahmed | C07D 307/36 549/429 |
| 8,263,792 B2 | 9/2012 | Robinson | |
| 9,359,650 B2 | 6/2016 | Pumesic | |
| 2005/0272134 A1 | 12/2005 | Hughes | |
| 2009/0194243 A1* | 8/2009 | Akhtar | D21C 3/04 162/76 |
| 2010/0029926 A1* | 2/2010 | Hoskins | C07D 307/06 536/56 |
| 2010/0216958 A1 | 8/2010 | Peters et al. | |
| 2010/0222626 A1 | 9/2010 | Nakamura | |
| 2011/0071306 A1* | 3/2011 | Robinson | C07C 43/137 549/488 |
| 2011/0073805 A1 | 3/2011 | Dibble et al. | |
| 2011/0087470 A1* | 4/2011 | Hames | G16B 5/00 703/2 |
| 2011/0137051 A1 | 6/2011 | Reunanen et al. | |
| 2011/0201084 A1* | 8/2011 | Wyman | C12P 7/10 435/262 |
| 2011/0250178 A1 | 10/2011 | Brooks et al. | |
| 2011/0311681 A1 | 12/2011 | Neufeld | |
| 2012/0270277 A1 | 10/2012 | Han et al. | |
| 2012/0322121 A1 | 12/2012 | Mosier et al. | |
| 2013/0078698 A1 | 3/2013 | Lali et al. | |
| 2013/0085255 A1 | 4/2013 | Coudray et al. | |
| 2013/0109869 A1* | 5/2013 | Sabesan | C07D 307/50 549/489 |
| 2013/0115661 A1* | 5/2013 | Peterson | C07C 27/00 435/126 |
| 2014/0107355 A1* | 4/2014 | Dumesic | C07D 307/68 549/485 |
| 2015/0176090 A1 | 6/2015 | Dumesic et al. | |
| 2019/0374929 A1* | 12/2019 | Wyman | B01J 23/72 |

FOREIGN PATENT DOCUMENTS

| | | |
|---|---|---|
| WO | 2011/063776 A2 | 6/2011 |
| WO | 2012097781 A1 | 7/2012 |

OTHER PUBLICATIONS

Cass (Industrial and Engineering Chemistry, vol. 40 No. 2, 216-219, 1948) (Year: 1948).*

Vanderlaan et al. (Biomass and Bioenergy vol. 14 No. 5/6, pp. 525-531, 1998) (Year: 1998).*

1-8, 12-23,25-27 and 29-36 (Year: 2009).*

Definition of glucan downloaded from https://collins.dictionary.com/english/glucan on Oct. 13, 2018 (Year: 2018).

Definition of aqueous downloaded from www.the freedictionary.com/aqueous+solution on Oct. 18, 2018 (Year:2018.

Amiri, Hamid et al., "Production of furans from rice straw by single-phase and biphasic systems", Carbohydrate Research, vol. 345, No. 15, Oct. 2010, pp. 2133-2138.

Baharlou, Simin, International Preliminary Report on Patentability and Written Opinion, PCT/US14/35506, Nov. 5, 2015.

Cai et al., "Solvent Systems for Enhanced Furfural and Hydroxymethyl Furfural (HMF) Production from Cellulosic Biomass," 2012 Sun Grant National Conference, New Orleans, Louisiana, pp. 1-39, Oct. 5, 2012.

Kokubo, Atsunori, Office Action, Japanese Patent Office, Application No. 2016-510804, Jan. 8, 2019.

Larsson et al., "The generation of fermentation inhibitors during dilute acid hydrolysis of softwood," Enzyme and Microbial Technology, vol. 24, pp. 151-159, 1999.

Vermeulen, Stephanie, Extended European Search Report, European Patent Office, Application No. 14788138.7, Oct. 16, 2016.

Waldron (ed.), "Bioalcoholl production Biochemical conversion of lignocellulosic biomass," Woodhead Publishing Series in Energy: No. 3, pp. 1-476, 2010.

Yao et al., Mokuzai Gakkaishi, "Soluble Properties of Liquefied Biomass Prepared in Organic Solvents I", vol. 40, No. 2, pp. 176-184 (1994).

Young, Lee W., International Search Report and Written Opinion, United States Patent & Trademark Office, PCT/US14/35506, Oct. 28, 2014.

* cited by examiner

Poplar Wood Solubilization by *C. thermocellum*

*C. therm.* CBP 2 (v/v) % Inoculum Size

| Material | Biomass | Temp (deg C) | Time (min) | Detail | Type | Glucan (%) | Xylan (%) | Lignin (%) | Solids Remaining after Pretreatment |
|---|---|---|---|---|---|---|---|---|---|
| A | Poplar | 160 | 25 | 0.5% H2SO4 | Dilute acid-only | 63.4 | 2.8 | 29.4 | 70.9125 |
| B | Poplar | 160 | 25 | 0.5% H2SO4 1:1 EtOH: Water | Organosolv | 80.7 | 3.8 | 11.5 | 54.525 |
| C | Poplar | 160 | 25 | 0.5% H2SO4 1:1 THF: Water | THF Co-solv | 87.2 | 2.8 | 6 | 44.725 |
| D | Poplar | 160 | 15 | 0.5% H2SO4 1:1 THF: Water | THF Co-solv | 85.8 | 3.4 | 7.5 | 48.1125 |
| Avicel | N/A | N/A | N/A | N/A | Control | 96.01 | 4.09 | 0.5 | N/A |

CO-SOLVENT TO PRODUCE REACTIVE INTERMEDIATES FROM BIOMASS

CROSS REFERENCE TO RELATED APPLICATIONS

This application is a continuation of U.S. application Ser. No. 14/787,090, filed Oct. 26, 2015, which application is a U.S. National Stage Application claiming priority under 35 U.S.C. § 371 to International Application No. PCT/US2014/035506, filed Apr. 25, 2014, which application claims priority to U.S. Provisional Application No. 61/816,713, filed Apr. 27, 2013, the disclosures of which are incorporated herein by reference in their entirety.

STATEMENT OF FEDERALLY SPONSORED RESEARCH

This invention was made with government support under DTOS59-07-G-00055 awarded by the Department of Transportation. The government has certain rights in the invention.

FIELD OF THE INVENTION

The disclosure is directed single phase aqueous co-solvent system for treating lignocellulosic biomass to extract lignin and produce reactive intermediates such as monomeric sugars, furfural, 5-HMF, and levulinic acid that are important renewable precursors for producing sustainable liquid transportation fuels and chemicals.

BACKGROUND

Declining petroleum supplies around the world have led to the increasing necessity to secure domestic oil supplies and develop an economic and highly effective renewable replacement for fossil fuels. Increased public awareness on the imbalance of atmospheric $CO_2$ emissions from the extensive use of non-renewable fossil fuels has put pressure on industrialized countries to demand the gradual integration of biomass-derived fuels into their transportation sectors. Lignocellulosic biomass is the most abundant resource of organic carbon on Earth and is the only renewable resource that is cheap enough to replace fossil fuels and sustain energy demands in the transportation sector. Such biomass is composed of three major polymeric components: cellulose, hemicellulose, and lignin. Cellulose is crystalline in structure and is comprised of linear β-1,4 linked glucose units known as glucan. Hemicellulose is amorphous in structure and is often primarily comprised of polymeric chains of β-1,4 linked xylose units known as xylan, a major hemicellulose component in most hardwood species, agricultural residues, and herbaceous energy crops. Lignin is a cross-linked heterogeneous complex covalently bonded to hemicellulose involving polymers of phenyl propanol units called monolignols. Only the maximum utilization of these three components from lignocellulosic biomass to produce reactive intermediates, including fuel precursors, will allow the economic production of biofuels to sustain current and future energy demands.

SUMMARY

The disclosure describes a method for biorefinery that maximizes the utilization of saccharides and carbonaceous material from all types of raw lignocellulosic biomass for the production of reactive intermediates at yields amenable for conversion to biofuels and biochemicals. The method involves a one-step reaction of raw cellulosic biomass using a single-phase mixture of aqueous tetrahydrofuran (THF). In some embodiments, the mixture further includes an acid catalyst. The biomass is incubated at a temperature of about 100° C. or greater. The reaction catalyzes and facilitates the production of hydrolyzed biomass sugars such as xylose and glucose and the like and the production of dehydration products from the hydrolyzed biomass sugars (e.g., furfural (FF), 5-hydroxymethylfurfural (5-HMF), and levulinic acid (LA)) and the removal of acid-insoluble lignin from the remaining unreacted hexose-rich solids. By changing the THF concentration, reaction temperature, reaction time, catalyst type, and catalyst loading, the product distribution can be altered between these reactive intermediates. This process is advantageous to other cellulosic pretreatment and conversion technologies due to the low operating and material cost of this one-step integrated single-phase approach, the high yields of dehydration and sugar products, the ease of scale-up as a batch or continuous process, the non-specific requirement of the cellulosic material used as feed, and the high recyclability of the low-boiling solvent.

The disclosure utilizes a water-miscible solvent, such as tetrahydrofuran, as a co-solvent in a one-pot reaction scheme to promote the targeted production of both primary and secondary reactive intermediates (RIs), such as monomeric sugars, furfural, 5-hydroxymethylfurfural, and levulinic acid, and isolated lignin, directly from lignocellulosic biomass. In some embodiments the THF co-solvent mixture is used in conjunction with an acid-based catalyst. Such reactive intermediates can be used as fuel precursors.

The disclosure provides a process where a co-solvent such as THF can be used in an integrated biorefinery process to enhance the production of reactive intermediates directly from lignocellulosic or cellulosic biomass. THF is a low boiling solvent that can be produced directly from furfural as a final co-product through catalytic decarbonylation to furan followed by hydrogenation.

The disclosure provides THF in a single phase solution with water and a suitable acid catalyst to promote the (1) fractionation and (2) deconstruction/solubilization of raw biomass and (3) enhance the production of RIs in a one-step catalytic conversion. THF as a co-solvent can (4) directly solubilize Klason-lignin as well as degradation tars that would normally accumulate without THF. By changing process conditions, (5) the solvent system can also allow the production a glucan-rich pretreated solid that can be more readily enzymatically hydrolyzed into fermentable glucose than that from typical pretreatment technologies or further thermochemically converted into more levulinic acid.

The disclosure provides a method for production of reactive intermediates from biomass, comprising: treating a biomass with a composition comprising a co-solvent mixture of aqueous THF under conditions to produce a solid glucan-rich material, monomeric sugars, furfural, 5-hydroxymethylfurfural and lignin products. The disclosure also provides a method for production of reactive intermediates from biomass, comprising: treating a biomass with a composition comprising a co-solvent mixture of aqueous tetrahydrofuran and an acid catalyst under conditions to produce a solid glucan-rich material, monomeric sugars, furfural, 5-hydroxymethylfurfural and lignin products. In one embodiment, the co-solvent mixture is monophasic at Standard Temperature and Pressure (STP). In another embodiment, the acid catalyst is selected from the group consisting of mineral acids, organic acids, and metal halide acids. In yet another embodiment, of either of the foregoing, the acid catalyst is sulfuric acid, hydrochloric acid, nitric acid, acetic acid, formic acid, trifluoroacetic acid, or FeCl$_3$. In another embodiment, the conditions include heating the combination of the biomass and composition to 100° C. to 220° C. In yet another embodiment the method further comprises removing and/or recovering THF from the liquid phase after co-solvent pretreatment of biomass. In yet another embodiment, the method further comprises removing and/or recovery of lignin from the co-solvent treated biomass by precipitation as a solid after the removal of THF from the liquid phase. In yet another embodiment, the method further comprises removing and/or recovering furfural from a liquid phase after co-solvent treatment of the biomass by azeotropic distillation or solvent extraction. In yet another embodiment, the method further comprises removing and/or recovering furfural from the vapor phase during and/or after co-solvent treatment by boiling and/or steam stripping. In another embodiment of the foregoing, the furfural is further processed to be catalytically upgraded to produce THF and/or methyl-THF. In another embodiment, the method further comprises recovering a liquid product comprising of C5 and C6 monosaccharides and/or their oligomers. In yet a further embodiment, the liquid product is neutralized by a base. In yet another embodiment, the method further comprises recovering a solid product after co-solvent treatment of biomass, wherein the solid comprises a glucan-rich material. In yet a further embodiment, the glucan-rich material is further treated with one or more enzymes that remove xylooligomers and higher chain length polymers of xylose to produce xylose monomers. In still another embodiment, the glucan-rich material is further treated with one or more enzymes that remove glucooligomers and higher chain length polymers of glucose to produce glucose monomers. In yet another embodiment, the glucan-rich material can be treated with a low boiling acids such as trifluoroacetic acid, formic acid, acetic acid and the like to produce glucose and related oligomers. In yet another embodiment, the glucan-rich solid is incubated with microorganisms and/or with added enzymes to produce an alcohol, fatty acids, or other products by fermentation. In another embodiment, the glucan material can be used to produce a micro-crystalline cellulose (MCC). In a further embodiment, the alcohol is ethanol. In still another embodiment, the alcohol contains 1 or more carbon molecules. In another embodiment, the microorganism is selected from the group consisting of a yeast, a bacteria, a mold, and a fungi. In still another embodiment, the microorganism is engineered to express a non-naturally occurring biosynthetic pathway for metabolizing a carbon source from the treated biomass to produce an alcohol, or other metabolite. In another embodiment, the glucan-rich material is used as paper pulp. In another embodiment, the lignin is further processed and captured by THF or dimethylsulfoxide (DMSO) as a liquid. In another embodiment, the acid catalyst is a Lewis Acid and/or Brønsted Acid. In yet a further embodiment, the acid catalyst is an acidic metal halide. In yet a further embodiment, the acidic metal halide is selected from the group consisting of AlCl$_3$, CuCl$_2$, CrCl$_3$, FeCl$_3$, and ZrOCl$_2$. In another embodiment, the aqueous THF co-solvent comprises a THF:water volume ratio of about 1:5 to about 7:1. In one embodiment, the treatment method lacks any salt or any added ionic salts. In another embodiment, the treatment method does not include any THF:water ratio of greater than 7:1 (e.g., less than 7:1, 6:1, 5:1 etc.).

The disclosure also provides a method for the combined fractionation and catalytic conversion of biomass to produce reactive intermediates from biomass, comprising: treating a biomass with a co-solvent mixture comprising THF, water, and an acid catalyst under conditions to produce furfural, 5-HMF, levulinic acid, glucan-rich material, and lignin. In one embodiment, the co-solvent mixture is monophasic at Standard Temperature and Pressure (STP). In another embodiment, the acid catalyst is selected from the group consisting of mineral acids, organic acids, metal halide acids, and solid acid catalysts. In yet another embodiment, the acid catalyst is selected from the group consisting of sulfuric acid, hydrochloric acid, nitric acid, formic acid, trifluoroacetic acid, FeCl$_3$, AlCl$_3$, CuCl$_2$ and any combination thereof. In still another embodiment, the conditions include heating the combination of the biomass and co-solvent mixture to 130° C. to 250° C. In one embodiment, a steam injection system is used to heat the reaction. In another embodiment, the method further comprises removing and/or recovering THF from the liquid phase after co-solvent treatment of the biomass. In another embodiment, the method further comprises removing and/or recovery of lignin from the co-solvent treatment of the biomass by precipitation as a solid after the removal of THF from liquid phase. In another embodiment, the method further comprises removing and/or recovering furfural and/or 5-HMF from a liquid phase of the co-solvent treatment of the biomass by distillation. In another embodiment, the method further comprises removing and/or recovery furfural from the vapor phase during and/or after co-solvent treatment by boiling and/or steam stripping. In another embodiment, the furfural is further processed to be catalytically decarbonylated and hydrogenated to produce THF. In another embodiment, the method further comprises extracting and/or recovering furfural and/or 5-HMF from a liquid phase of the co-solvent treatment of the biomass by a water-immiscible organic solvent. In another embodiment, the immiscible organic solvent is an ether, ketone, alcohol, alkane or any combination thereof. In another embodiment, the method further comprises recovering a solid product after co-solvent treatment of the biomass, wherein the solid comprises a glucan-rich material. In another embodiment, the glucan-rich material is further treated with one or more enzymes that remove glucooligomers and higher chain length polymers of glucose to produce glucose monomers. In a further embodiment, the glucan-rich solid is incubated with microorganisms and/or enzymes to produce an alcohol or other fermentation product. In still a further embodiment, the glucan-rich solid is further catalytically converted to 5-HMF and/or levulinic acid. In another embodiment, the lignin is further processed and captured by THF or DMSO as a liquid. In another embodiment, the acid catalyst is a Lewis Acid or Brønsted Acid. In yet another embodiment, the acid catalyst is a metal halide acid. In another embodiment, the metal halide acid is selected from the group consisting of AlCl$_3$, CuCl$_2$, CrCl$_3$, FeCl$_3$, and ZrOCl$_2$. In one embodiment, the THF:water volume ratio is about 1:1 to about 7:1. In one embodiment, the treatment method lacks any salt or any added ionic salts. In another embodiment, the treatment method does not include any THF:water ratio of greater than 7:1 (e.g., less than 7:1, 6:1, 5:1 etc.).

The disclosure also provide a system for carrying out the methods described herein. In one embodiment, the system comprises a vessel for mixing a biomass with a co-solvent aqueous THF solution. One or more fluidly connected valves and tubes can be used to transport treated biomass to additional vessels for separation of solids and liquids. Such additional vessels or chambers can include heating elements, sedimentation systems and the like (see, FIG. 2A-D).

The disclosure also provides a composition comprising a biomass and a THF aqueous co-solvent. In one embodiment, the composition can further include an acid catalyst. In another embodiment, the THF aqueous co-solvent comprises a THF:water volume ratio of about 1:3 to about 7:1. In another embodiment, the acid catalyst is a Lewis acid. In a further embodiment, the Lewis acid is sulfuric acid. In another embodiment, the acid catalyst is a metal halide acid. In another embodiment, the acid catalyst is a Brønsted acid. In a further embodiment, the metal halide acid is selected from the group consisting of $AlCl_3$, $CuCl_2$, $CrCl_3$, $FeCl_3$, and $ZrOCl_2$.

Other features and advantages of the invention will become apparent from the following detailed description, taken in conjunction with the accompanying drawings, which illustrate, by way of example, the features of the invention.

DETAILED DESCRIPTION

Figure 1:
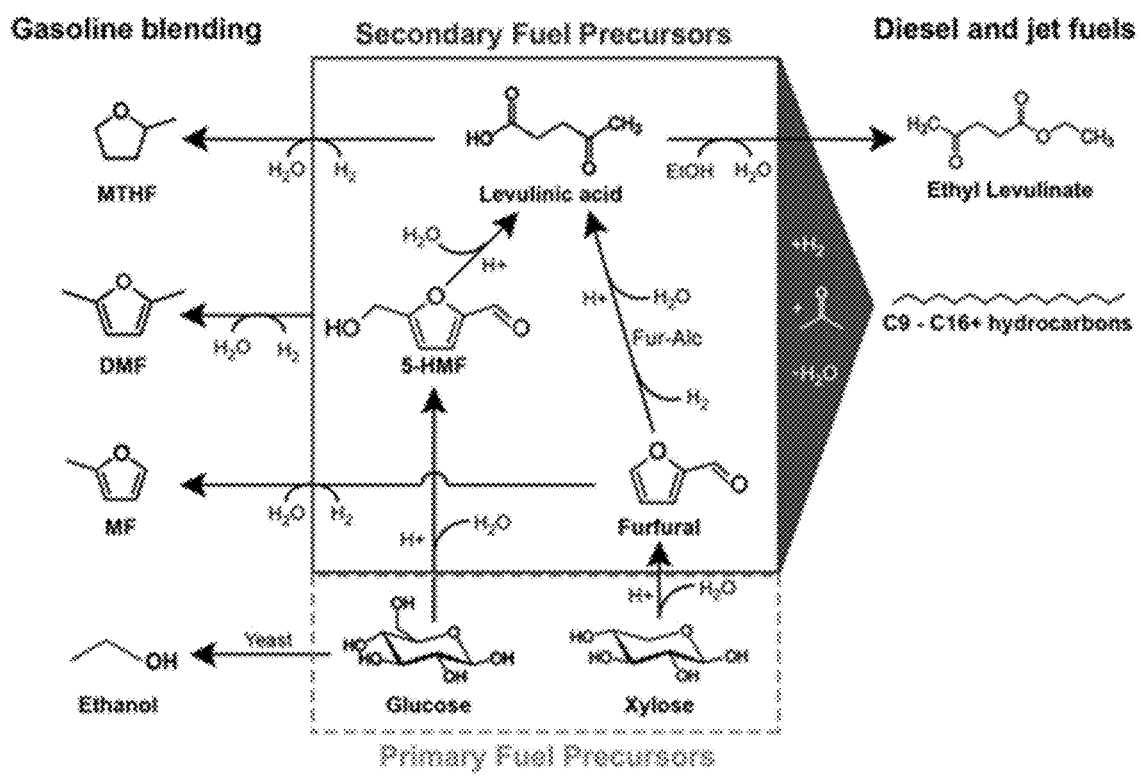
FIG. 1 shows a reaction network illustrating primary and secondary reactive intermediates for production of ethanol and gasoline, jet, and diesel range aromatic and hydrocarbon fuels. 5-HMF: 5-hydroxymethylfurfural; MF: 2-methylfuran; DMF: 2,5-dimethylfuran; MTHF: 2-methyltetrahydrofuran; Fur-Alc: furfuryl alcohol.

As used herein and in the appended claims, the singular forms "a," "and," and "the" include plural referents unless the context clearly dictates otherwise. Thus, for example, reference to "an enzyme" includes a plurality of such enzymes and reference to "the material" includes reference to one or more materials known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The extensive use of non-renewable fossil fuels in the last half-century has strained world petroleum supplies and the environment. As a result, US and European countries have pushed for the use of biofuels in their transportation sectors to alleviate foreign energy dependence and environmental concerns. Although corn ethanol has been the most commercially successful biofuel in the US, sustainability concerns over the growth and supply of corn have necessitated a redirection of focus towards production of fuels from lignocellulosic feedstocks. Lignocellulosic biomass is the most abundant resource of organic carbon on Earth and is a renewable resource that can economically replace fossil fuels for production of liquid fuels and sustain future energy demands in the transportation sector. A feasible conversion strategy requires efficiently overcoming the recalcitrance of lignocellulose to maximize the yield of reactive sugar intermediates and their derivatives that are suitable for transformation to final products by targeted conversion technologies. In this context, a reactive intermediate (RI) as used herein includes any sugar or sugar dehydration product that can be biologically, chemically, or catalytically converted into fuels and chemicals.

Cellulosic and lignocellulosic biomass residues and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic biomass residues and wastes, composed of carbohydrate polymers comprising cellulose, hemicellulose, and lignin can be generally treated by a variety of chemical, mechanical and enzymatic means to release primarily hexose and pentose sugars, which can then be fermented to useful products including ethanol or dehydrated by acids to furfural, 5-HMf, and levulinic acid, which can then be catalytically upgraded to gasoline, diesel, and jet range fuels.

Pretreatment methods are used to make the carbohydrate polymers of cellulosic and lignocellulosic materials more readily available to saccharification enzymes or acid catalysts. Standard pretreatment methods have historically utilized primarily strong acids at high temperatures; however due to high energy costs, high equipment costs, high pretreatment catalyst recovery costs and incompatibility with saccharification enzymes, alternative methods are being developed, such as enzymatic pretreatment, or the use of acid or base at milder temperatures where decreased hydrolysis of biomass carbohydrate polymers occurs during pretreatment, requiring improved enzyme systems to saccharify both cellulose and hemicellulose. For example, typical acid catalyzed or hydrothermal (water-only) pretreatments that present the least expensive pretreatment options are less effective on more recalcitrant lignocellulosic feedstocks such as hard and soft woods. This means that higher enzyme loadings are necessary to achieve higher sugar recovery yields that significantly increase the costs of the process. The presence of lignin has also been long regarded as an inhibitor to enzymes and its effective removal without significantly reducing the porosity of the pretreated material has been shown to significantly reduce the enzyme loadings necessary for high sugar recovery. Thus, there is still a need for a more feedstock agnostic pretreatment process that can simultaneously delignify the biomass, promote biomass solubilization, and achieve high total sugar yields with as little or no enzyme as possible.

FIG. 1 outlines a reaction network for the production of ethanol and gasoline, jet, and diesel range fuel products from primary and secondary reactive intermediates. As shown, xylose from hemicellulose and glucose from cellulose can be fermented to ethanol or dehydrated with acid catalysts to produce the secondary reactive intermediates such as furfural and 5-HMF. Further 5-HMF hydrolysis results in equimolar formation of more stable products levulinic acids (Las) and formic acid. LA can also be synthesized from furfural by a furfuryl alcohol intermediate. These secondary reactive intermediates can be catalytically upgraded into potential fuel products by selective hydrogenation over metal-based solid catalysts. As shown, catalytic hydrogenation of furfural and 5-HMF produces promising gasoline blending products 2-methylfuran (MF, 131 Research Octane Number RON) and 2,5-dimethylfuran (DMF, 119 RON), respectively. 2-methyltetrahydrofuran (MTHF, 86 RON) can be produced from hydrogenation of LA and ethanol can be produced from sugars by yeast and/or bacteria fermentation, both of which are primary components in P-series biofuels. Ethanolysis of LA produces ethyl levulinate (EL), a diesel blendstock, whereas aldol-addition using acetone and hydrodeoxygenation of secondary reactive intermediates with hydrogen can produce longer-chained hydrocarbon fuels of up to 16 carbon lengths for jet and diesel applications.

Alternatively, reactive intermediates such as furfural, hydroxymethylfurfural, and levulinic acid, which are formed during the acid catalyzed pretreatment of cellulosic biomass, can be hydrogenated and hydrodeoxygenated into alkanes that are compatible with the existing fuel infrastructure ("drop-in" fuels) by the action of heterogeneous catalysts (Xing et al. 2010 and Huber et al. 2005). These RIs can be produced at higher concentrations from raw biomass by additional heating and the action of an acid catalyst in aqueous conditions (Zeitsch 2000). FIG. 1 depicts the hydrolysis and dehydration pathways for glucan and xylan to form RIs (see also scheme 1). In the pentose pathway, xylan is first hydrolyzed into xylose, which is then dehydrated with the removal of three water molecules to form furfural. Further dehydration of furfural at high temperatures will produce formic acid. Similarly for the hexose pathway, glucan is hydrolyzed into glucose, which then dehydrated to form HMF. HMF is highly unstable in an aqueous environment and will rapidly breakdown to equimolar amounts of levulinic acid and formic acid until the HMF is consumed (Karinen 2011).

SCHEME 1

Pentose Hydrolysis and Dehydration Reaction Pathway

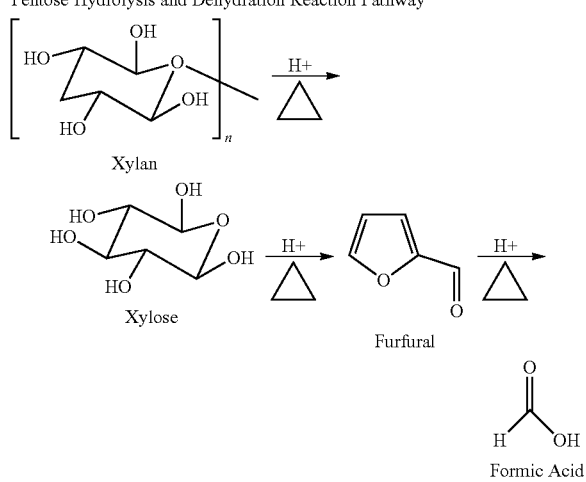

Hexose Hydrolysis and Dehydration Reaction Pathway

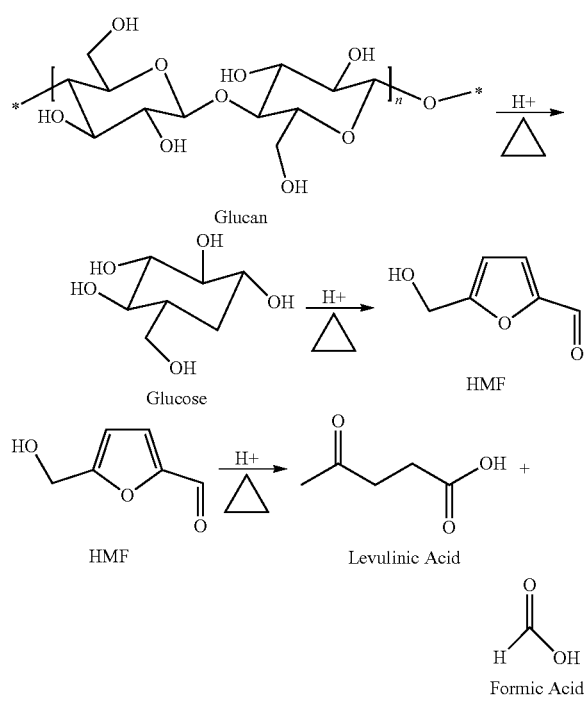

Furfural is a heterocyclic aldehyde that is made from agricultural raw materials rich in pentosans and is useful as a furanic precursor. The maximum theoretical yield of furfural that can be obtained from xylan is 0.7273. Since pentosan hydrolysis occurs at a much faster rate than the formation of furfural from a pentose sugar, the kinetics of hydrolysis can be mostly disregarded in the optimization of furfural production. Because arabinose typically follows the same reaction pathway as xylose, it is reasonable to approximate that all the pentosan content in most biomass types except softwoods is xylan (Zeitsch 2000). Because furfural can degrade under an aqueous environment by self-resinification or condensation with a pentose-to-furfural intermediate, removing furfural from the catalytically active phase by vaporization can prevent these loss reactions from occurring (Zeitsch 2000). Currently, furfural is produced predominantly in China from various agricultural wastes at reported yields of less than 50%, with higher yields owing to the continuous removal of furfural by steam stripping (Win 2005). Continuous distillation following steam stripping allows for product purity of up to 99.5% (Win 2005).

HMF is the 6-carbon analog of furfural with an additional alcohol group on a branched carbon. It can be produced by dehydration from either fructose or glucose with higher yields from the former (Karinen 2011). The maximum theoretical yield of HMF from glucan is 0.7785. Due to the less stable ring structure of fructose than glucose, the formation of HMF is faster from fructose. Further hydrolysis of HMF in the aqueous phase leads to levulinic acid and formic acid, which are stable species with no further hydrolysis products (Kuster 1990). Levulinic acid is also considered an important platform chemical for biofuel synthesis (Dautzenberg 2010; Werpy and Peterson 2004).

Improving the yields of furfural and HMF necessitates their protection from the catalytically active aqueous phase or the application alternative reaction mechanisms.

RIs such as furfural and levulinic acid, that can be made directly from biomass sugars, are useful building blocks for the production of high-value chemicals and fuels. Gasoline and diesel-range alkanes can be catalytically produced from these RIs, and continued efforts to improve their synthesis have made this pathway attractive as an industrially relevant biofuels platform. Furfural is of interest as it is one of the only natural precursors to furan-based chemicals and is commercially produced at low yields (50 mol %) from xylan-rich lignocellulosic residues today.

Ongoing advances in catalysis have improved the selective conversion of secondary reactive intermediates to so-called drop-in fuel products that are compatible with the existing fuel infrastructure, but obtaining high overall reactive intermediate yields directly from lignocellulosic biomass has been a long-standing barrier. Thus, there is a pressing need to develop effective strategies that integrate catalytic conversion with biomass deconstruction to co-produce FPs from both C5 and C6 sugars in order for biomass drop-in fuels to have impact. Achieving high overall product yields from the major biomass fractions hemicellulose, cellulose, and lignin in an integrated process has the highest potential to enable future biomass-to-fuel technologies. Various acid catalyzed co-production schemes from biomass have been proposed including co-producing furfural with levulinic acid, furfural with 5-HMF, furfural with cellulose, and LA from both furfural and 5-HMF, but many suffer from low yields due to the complex heterogeneous nature of biomass. For example, furfural and 5-HMF produced early in biomass deconstruction are rapidly degraded before sufficient LA yields from C6 sugars can be achieved. Consequently, LA production and recovery would have to follow furfural removal, thereby necessitating multistage reactions with independent product recovery steps, expensive steam stripping to remove furfural, use of corrosive mineral acids, and/or biphasic reactions. Alternatively, co-production of furfural and 5-HMF would appear more desirable as both products could be recovered together by a suitable extracting solvent and simultaneously converted into "drop-in" fuels such as MF and DMF by a single catalyst.

Furfural is typically synthesized from the acid-catalyzed dehydration of C5 sugars (arabinose and xylose) whereas levulinic acid can be made from either C5 or C6 sugars (glucose, galactose, and mannose). Water-soluble Brønsted acids (e.g., acid catalysts) such as HCl and $H_2SO_4$ have typically been used to catalyze such dehydration reactions, but homogeneous and heterogeneous solid catalysts have also been applied successfully.

Various extracting solvents have been used to improve RI production by reducing side reactions that would occur in water. Yield improvements have been shown in biphasic systems for which the starting material was either extracted or pure sugars. In lignocellulosic biomass, C5 sugars in hemicellulose are more rapidly hydrolyzed and dehydrated than C6 sugars in cellulose and achieving high yields of RIs from both cellulose and hemicellulose fractions simultaneously in a biphasic system would be challenging as furfural degrades long before sufficient LA yields are achieved. In addition, it may be difficult to maintain two discernible liquid phases at the high solids concentrations needed for reasonable thermal loads. Thus, a single-phase process that separates the hemicellulose, cellulose, and lignin fractions while achieving high product yields from all fractions would be useful. Combining pretreatment and enzymatic and/or catalytic hydrolysis is shown here to be a promising approach for extracting cellulosic sugars, and xylose conversion into furfural.

The major routes to converting cellulosic biomass into biofuels include gasification of biomass to syngas and subsequent Fischer-Tropsch synthesis, pyrolysis and liquefaction of biomass to bio-oils, aqueous phase catalytic processing of sugars dehydration compounds, and sugar hydrolysis by pretreatment followed by enzymatic hydrolysis of solids residue for microbial fermentation (Yang and Wyman 2008). Process yields, production costs, and feedstock availability are key limitations to these routes, and high product yields must be achieved from biomass sugars, while using the simplest process that is effective for many feedstock types. For biological conversion, raw biomass needs to be pretreated to maximize the accessibility and utilization of the sugars. Pretreatment technologies, such as with dilute acid, can recover pentose sugars from hemicellulose with high yields and reduce the recalcitrance of the remaining cellulose fraction. Acid neutralization must follow dilute acid pretreatment and the presence of non-sugar byproducts can inhibit downstream biocatalysts.

This disclosure provides for the use of tetrahydrofuran (THF), a polar cyclic ether, as a miscible co-solvent in aqueous solution with or without an acid catalyst for the purpose of pretreating lignocellulosic biomass. The disclosure provides that THF in a single phase aqueous mixture (as a co-solvent) is extremely effective at performing the solubilization, fractionation, and pretreatment of lignocellulosic biomass to achieve high yields of total sugars and extracted lignin product for their efficient conversion into renewable chemicals and fuels. THF co-solvent pretreatment is beneficial over competing pretreatment technologies in at least the following ways: (1) THF co-solvent promotes the solubilization of hemicellulose and cellulose fractions and catalyzes their hydrolysis to directly obtain high yields of C5 and C6 sugars at lower severities than leading pretreatments such as using water-only, dilute acid-only, or Organosolv; (2) THF co-solvent pretreatment dramatically improves the accessibility of lignocellulosic biomass to saccharification enzymes allowing higher total yields of C5 and C6 sugars to be obtained at lower enzyme loadings and reaction severities than dilute acid-only pretreatment; (3) THF co-solvent can dissolve and depolymerize nearly all the lignin (over 90% delignification) to be effectively recovered by precipitation from the liquid phase upon removal of THF; (4) THF co-solvent can be used with mineral acids, organic acids, metal salt acids, and base catalysts to tune the product distribution for various co-production schemes; (5) pretreated material from reaction with THF co-solvent can be used as direct feed for biological fermentation (such as, but not limited to, simultaneous saccharification and fermentation SSF or consolidated bioprocessing CBP) to produce fuel products such as ethanol at higher yields than dilute acid-only pretreated material; (6) THF in the co-solvent system can be easily recovered by low temperature or vacuum distillation for reuse, and (7) THF is renewable and can be synthesized by the hydrogenation of furfural that is the direct acid dehydration product of pentose sugars from biomass.

As used herein a "THF co-solvent" or "co-solvent" refers to a medium wherein the co-solvent medium is monophasic (e.g., single-phase) at Standard Temperature and Pressure (STP) and contains an aqueous medium and THF. The relative ratios of, for example, water and THF can range from 1:5 to 7:1 THF:water.

As used herein an "acid catalyst" generally refers to a water-soluble acid. In various embodiments, the acid catalyst is selected from the group consisting of a mineral acid, a metal-halide acid, a heteropolyacid, an organic acid, or a combination thereof. In one embodiment, the acid catalyst is a mineral acid selected from the group consisting of phosphoric acid, sulfuric acid, hydrochloric acid, and any combination thereof. In another embodiment, the acid catalyst is an organic acid selected from the group consisting of acetic acid, an alkyl sulfonic acid, an aryl sulfonic acid, formic acid, a halogenated acetic acid, a halogenated alkylsulfonic acid, a halogenated aryl sulfonic acid, oxalic acid, and any combination thereof. Various metal-halide acids are known and include, for example, $AlCl_3·6H_2O$, $CuCl_2·2H_2O$, $CrCl_3·6H_2O$, $FeCl_3·6H_2O$ and $ZrOCl_2·8H_2O$ The disclosure provides a one-pot reaction scheme where a single-phase solvent mixture of, for example, water, tetrahydrofuran, and a mineral acid at a temperature of about 100° C. or more will catalyze and facilitate the production of furanic compounds from the hydrolyzed biomass sugars and the removal of acid-insoluble lignin from the remaining unreacted solids. The purpose of the invention is to use the single phase solvent mixture to (1) hydrolyze all of the pentosans and some of the hexosans from raw lignocellulosic biomass into their respective monomeric sugars, (2) catalyze the dehydration of the resulting monomeric sugars into furfural (FF), hydroxymethylfurfural (HMF), levulinic acid (LA), and formic acid (FA) at high yields, (3) dissolve and extract the acid-insoluble Klason lignin from the biomass into the liquid fraction for their later conversion into high-value byproducts, and (4) generate an easily hydrolysable hexose-rich solid fraction that can be used for enzymatic digestion, fermentation, or chemical conversion. From the outcomes of the results shown below, there is sufficient evidence that the purposes 1-4 can be achieved in a relevant biorefinery setting.

The disclosure demonstrates the use of tetrahydrofuran (THF) as both a co-solvent and final product in an integrated biorefinery process to enhance the production of furfural and other RIs from biomass. THF is a low boiling solvent that can be produced industrially from the cyclization of 1,4-butanediol and recovered as an azeotrope with water. However, it can also be synthesized directly from furfural through catalytic decarbonylation to furan followed by hydrogenation. THF is a versatile extracting solvent that has favorable properties for enhancing furfural yields from extracted hemicellulosic sugars and raw biomass in a biphasic environment. However, THF is naturally miscible with water and would need to be saturated with solute to form an independent phase. The disclosure demonstrates that application of THF in a single phase solution with water and a catalysts (e.g., an acid catalyst such as a mineral acid catalyst (e.g., sulfuric acid ($H_2SO_4$) or nitric acid), a metal halide acid catalyst (e.g., $FeCl_3$), or an organic acid (e.g., acetic acid or formic acid)) provides for a one-step catalytic conversion of raw maple wood to fractionate the biomass and produce a combination of C5 and C6 monosaccharides, furfural, 5-HMF, and levulinic acid at high yields depending on reaction conditions and catalyst used. The THF co-solvent was also able to directly solubilize Klason lignin from raw maple wood as well as degradation tars that would normally accumulate without THF. As a result, the solvent system also produces a glucan-rich pretreated solids fraction that can be more readily enzymatically hydrolyzed into fermentable glucose than that from typical pretreatment technologies or further can be chemically converted to additional levulinic acid.

The data below demonstrate that THF is an exceptionally effective single phase co-solvent for integrated biomass reactions that enhance reactive intermediate yields during biomass deconstruction, as well as delignification. For example, using dilute sulfuric acid in a miscible solution of THF and water, higher overall yields of furfural, 5-HMF, and LA were achieved from maple wood than in prior reactions conditions. However, because sulfuric acid favors furfural and LA production, tuning of this co-solvent system with different catalysts was examined and demonstrated to improve yields for co-production of furfural and 5-HMF. Because aqueous monophasic reactions with dilute mineral acids typically suffer from low 5-HMF yields as it readily hydrolyzes to form LA and formic acid, methyl isobutyl ketone (MIBK) was employed as an extracting solvent in a biphasic reaction, but solvent recovery was an issue and the high energy requirements for heating and stirring and limited effective solids loading of a biphasic reaction for large scale fuel production from solid biomass would likely hinder its commercial appeal. Thus, a single phase reaction is beneficial if a more selective acid catalyst is used to improve selectivity of biomass glucan to 5-HMF instead of LA.

Metal halides are inexpensive acid catalysts that are well studied for selectively promoting alternate reaction mechanisms of xylose to furfural and glucose to 5-HMF compared to traditional mineral acids. In analogous pathways, aldose-to-ketose isomerization of glucose to fructose and xylose to xylulose was observed in the presence of certain bi- and trivalent metal cations that can more easily undergo acid-catalyzed dehydration. However, evidence also suggests that the strong Lewis acid character of metal halides accelerates several competing loss reactions that could potentially decrease product yields. When used in biphasic and expensive ionic-liquid co-solvent systems, metal halides demonstrated good performance with pure sugars but poor performance on cellulose and biomass, necessitating additional biomass pretreatment.

Thus, the disclosure also demonstrates that metal halide acid catalysts in combination with THF is as a miscible co-solvent that significantly improves yields for co-production of both furfural and 5-HMF from lignocellulosic biomass such as shown with maple wood and corn stover. In this way, biomass pretreatment and catalytic dehydration of soluble sugars can be performed in a one-pot reaction. Exemplary metal salt acid catalysts $AlCl_3$, $CuCl_2$, $CrCl_3$, $FeCl_3$, and $ZrOCl_2$ can be used. For example, each of the foregoing metal salt acid catalysts was studied for sugar conversion and selectivity for furfural, 5-HMF, and LA production by applying the co-solvent system to pure sugars. By using metal halide catalyst, the reaction severity and solvent (THF) loadings can be optimized for scale to achieve the highest co-production of furfural and 5-HMF yields. The results reveal how different Brønsted and Lewis acids can be applied in the THF co-solvent reaction strategy to maximize overall yields of furanic products for a biorefinery process.

The disclosure demonstrates that metal halides are non-corrosive and highly selective acid catalysts suitable for co-production of furfural and 5-HMF directly from lignocellulosic biomass without a separate pretreatment step. The disclosure demonstrates that coupling metal halides with THF as a green co-solvent in a highly effective single phase conversion strategy provide useful co-production yields of furfural and 5-HMF directly from biomass, producing a clean product stream suitable for catalytic hydrogenation to final fuel products. Screening of several promising metal halides $AlCl_3 \cdot 6H_2O$, $CuCl_2 \cdot 2H_2O$, $CrCl_3 \cdot 6H_2O$, $FeCl_3 \cdot 6H_2O$, and $ZrOCl_2 \cdot 8H_2O$ on the basis of sugar conversion and selectivity to secondary reactive intermediates demonstrated that $FeCl_3$ performed best in the THF co-solvent system owing to its high Brønsted acidity and moderate sugar conversion rate.

The ratio of THF and water by volume can be adjusted in the system and can range from 1:5 to greater than 7:1 THF:water (e.g., 1:4, 1:3, 1:2, 1:1, 2:1, 3:1, 4:1, 5:1, 6:1, 7:1 etc. vol:vol). In addition, the percentage of the acid catalyst can be varied to optimize the desired production, based upon the amount of biomass, the desired product, temperature and THF:water ratio. For example, the range of acid catalyst loading needed for THF co-solvent pretreatment range of 0 wt % to 10 wt % depending on the type of acid. In another example, a 4:1 THF:water ratio and 1 wt % $FeCl_3$ co-solvent reaction achieved 95% yield of furfural and 51% yield of 5-HMF directly from maple wood and similar yields from corn stover after 60 min reaction at 170° C. By decreasing the concentration (or volume contribution) of THF in the reaction, one can tune biomass solubilization to increase the product mass of a glucan-rich solid residue that is suitable for further catalytic reaction, enzymatic digestion, or a potential pulp and paper product. During the co-solvent reaction, THF extracted over 90% of the lignin from biomass that could be recovered as a fine powder. Due to its low boiling point, THF was recovered by room temperature vacuum distillation. Furfural and 5-HMF can be concentrated by an immiscible extracting solvent and the catalyst can be recycled in the aqueous stream.

The disclosure also contemplates the use of THF co-solvent pretreatments in batch, continuous flow-through, or plug flow configurations for either (A) traditional pretreatment of biomass followed by enzymatic hydrolysis or (B) direct solubilization of biomass to recover sugars without the need for an enzymatic hydrolysis step. In the latter case (B), THF co-solvent can be applied to a heated flow-through reactor at >1:1 THF:water ratios with little or no acid to effectively solubilize biomass and release mono- and oligo-saccharides that are then concentrated by the removal and recovery of THF. The total sugar yields (stage 1+stage 2) for typical pretreatments is calculated by the addition of total soluble sugar yield (C5+C6 sugars) released after the heated reaction (stage 1, pretreatment) and the total sugar soluble yield released after treatment of the pretreated solids with saccharification enzymes (stage 2). Due to their overwhelming majority in biomass composition, it is generally safe to assume all C5 sugars as xylose and all C6 sugars as glucose.

Sugars can be quantified by High Pressure Liquid Chromatography (HPLC). Total lignin is calculated by the mass of total lignin precipitated upon recovery of THF solvent whereas delignification is calculated by the percentage of lignin remaining in the pretreated material over the initial lignin content of the raw material.

The cellulosic material used as a biomass source can be any material containing cellulose. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue. The cellulosic material can be any type of biomass including, but not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, Applied Biochemistry and Biotechnology 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix.

Optimization of the methods of the disclosure can be achieved by adjustment of the reaction temperature, the amount, type, condition, and particle size of the raw biomass, the type and concentration of the acid involved, and the ratio of THF to water in the solvent water mixture. The application of this invention in a continuous process where the product and solvent are continuously removed can further improve the yields of the RIs and allow for better integration into a large scale production process. Furfural is also a known chemical precursor to THF manufacture and the integration of this invention with a downstream catalytic hydrogenation process can supply the THF needed in the reaction as well as provide a potential platform for biochemical and biofuel production. The resulting hexosan rich solid fraction from the process may be enzymatically digested to yield fermentable hexose sugars or used as a direct feed to Simultaneous Saccharification and Fermentation (SSF) and Consolidated Bioprocessing (CPB) processes. After the solvent is recycled, the remaining lignin can be precipitated and used for producing novel aromatic compounds or carbon-based compounds such as carbon fiber or carbon nanotubes.

Figure 2A:
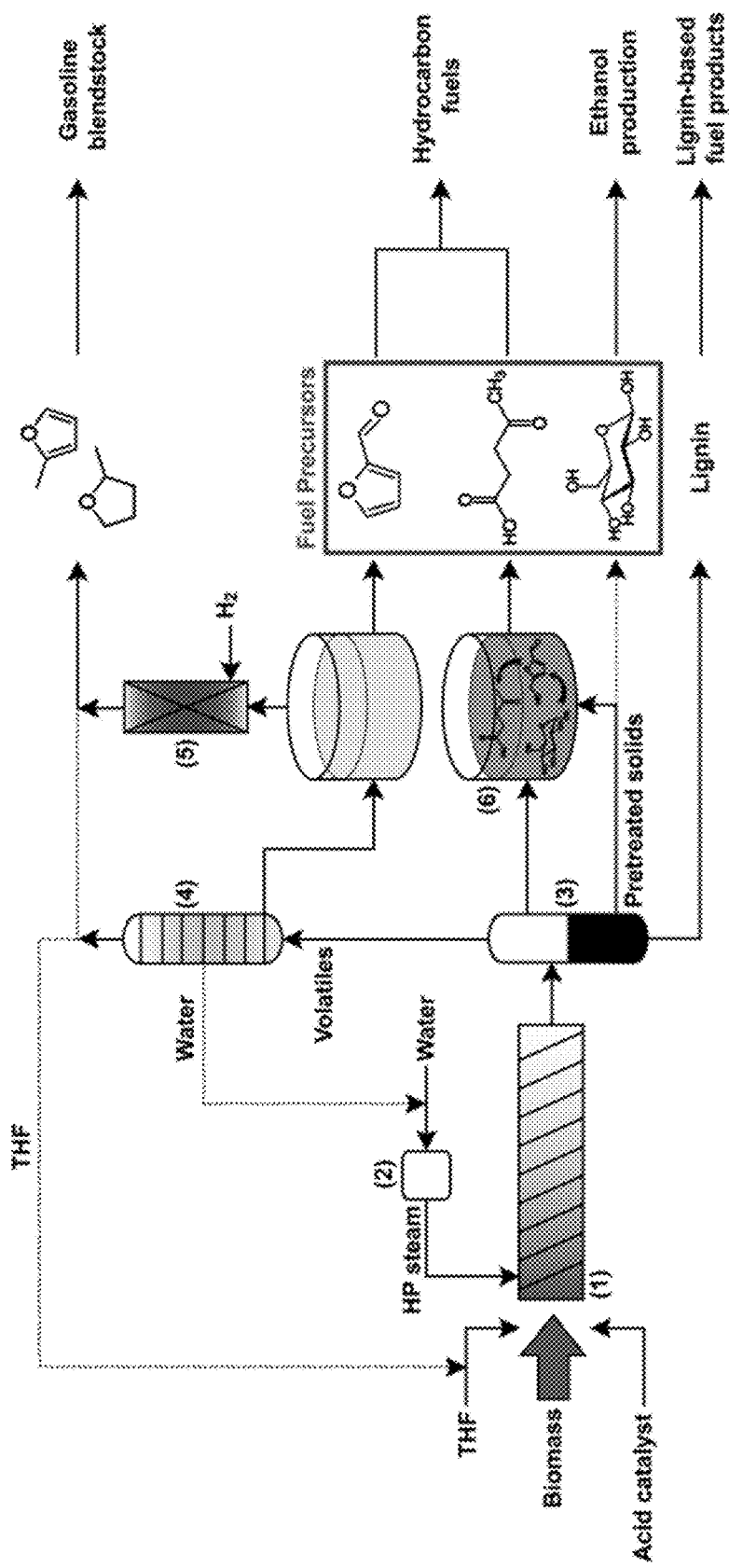
FIG. 2A-D are schematic of exemplary processes of the disclosure. (A) Conceptual process flow diagram of an approach to produce reactive intermediates and isolated lignin from lignocellulosic biomass using THF as a single-phase co-solvent to enhance biomass fractionation and product yields. Process key: (1) High solids screw-type Pandia reactor, (2) High pressure (HP) boiler (3) Removal of volatiles and solids separation (4) Continuous azeotropic distillation to recover furfural, THF, and water, (5) Catalytic upgrading and hydrogenation of furfural, and (6) levulinic acid production of remaining glucose and glucan-enriched material in a concentrated solution. Dotted lines represent recycle and recovery streams. (B) Simplified process diagram of a proposed use of THF co-solvent strategy for direct conversion of lignocellulosic biomass to co-produce furfural and 5-HMF for catalytic upgrading to aromatic fuel products. Furfural and 5-HMF will be extracted by an organic solvent and hydrogenated (blue box, right) to produce aromatic fuels such as MF and DMF. Lignin is precipitated upon recovery of THF. (1) Organic stream containing furfural and 5-HMF (2) Aqueous stream containing metal halide catalyst, furfural and 5-HMF. (C) Simplified process diagram of a proposed use of THF co-solvent strategy for the pretreatment of lignocellulosic biomass to hydrolyze C5 and C6 sugars at high yields followed by simultaneous saccharification and fermentation (SSF) of the C5 and C6 sugars to ethanol (or other alcohols) at high yields. In the first pretreatment step (Stage 1), THF co-solvent reaction hydrolyzes all the hemicellulose sugars into the liquid phase as liquid products, extracts over 90% of the acid-insoluble lignin as a highly oxidized THF-soluble lignin product, and produces a glucan-rich pretreated solid that is highly digestible by enzymes. The pretreated solids or solid products are then separated from the liquid products and washed to remove any water-soluble contaminants. The THF is then recovered and removed from the liquid stream to be recycled back into the first reaction step. Upon removal of THF, the extracted lignin product can be recovered as a solid precipitate. The liquid stream is then neutralized by a base such as calcium hydroxide, ammonium hydroxide (or equivalent) to be compatible for fermentation. The liquid products and solid products are then fed to a fermentor (Stage 2) where a micro-organism and saccharification enzymes are introduced to biologically convert the solid and liquid products into ethanol or other alcohol. (D) Shows a simplified process flow diagram of a possible continuous approach to produce reactive intermediates and isolated lignin from lignocellulosic biomass using THF as a single-phase co-solvent to enhance biomass fractionation and product yields. Process key: (1) High solids screw-type reactor, (2) High pressure (HP) boiler (3) Removal of volatiles and solids separation (4) Continuous distillation to purify products, (5) Catalytic upgrading and hydrogenation of furfural, and (6) Continuous levulinic acid production of glucan-enriched material in a more concentrated acid solution. Dotted lines represent recycle and recovery streams.

FIG. 2A depicts a process outline that shows one possibility for the efficient production of FPs and isolated lignin using the disclosed co-solvent system. Since THF is miscible in the aqueous phase, a higher solids loading can be achieved for greater thermal efficiency compared to a two phase system. Optimization of the highest % solids will be determined by the type and moisture content of the raw feedstock and the processing equipment options. As shown in FIG. 2A, raw biomass is first combined into a mixture containing the co-solvent (in this case THF), water, and an acid catalyst. The slurry is then fed into a screw-type Pandia reactor, designated in FIG. 2A by (1), much like the ones used in the 1960s for continuous furfural production, to keep residence times reasonably uniform and minimize unnecessary by-product formation. Rapid reactor heat up is provided by high-pressure (HP) steam from an HP boiler (2). The hot slurry is quickly released at the reactor exit into a separation unit (3). In this step, water-volatile components, such as furfural and THF, can be flashed along with steam to a distillation unit (4). The THF azeotrope contains only about 4.6 wt % water so its recovery at this composition is not demanding as additional drying is unnecessary. The dotted lines from (4) in FIG. 2A show the THF and water recycle streams. 5-HMF and LA are not volatilized with the water and are concentrated with some hydrolyzed glucose in the remaining aqueous layer in (3). For recovery of HMF and LA, solvent extraction or vacuum distillation can reduce unwanted reactions. However, if only LA production is desired, the concentrated aqueous solution can be sent directly to a second continuous reactor (6) for a higher temperature reaction. The removal of THF from the liquid phase following the reaction causes the dissolved lignin to precipitate as a solid residue. Due to its sticky nature, a suitable solvent is likely needed to re-dissolve the extracted lignin for further processing and catalytic upgrading into fuel or chemical products. In line with this, pure THF readily re-dissolves the recovered lignin. Assuming an efficient continuous device is available to effectively separate the remaining glucan-rich solid fraction, the solids can be washed, neutralized, and enzymatically hydrolyzed into fermentable glucose or used as processed feed for SSF or CBP operations. This approach has an added benefit that the combination of high severity reaction conditions with lignin removal make the resulting solids more easily hydrolyzed with low enzyme doses than has been achieved with other pretreatment systems that are constrained by the need to use low severities to avoid large loses of xylose to furfural when xylose fermentation is targeted. Or, the glucan-rich material can be directly sent to a second high temperature reactor for additional LA production (6).

Figure 11:
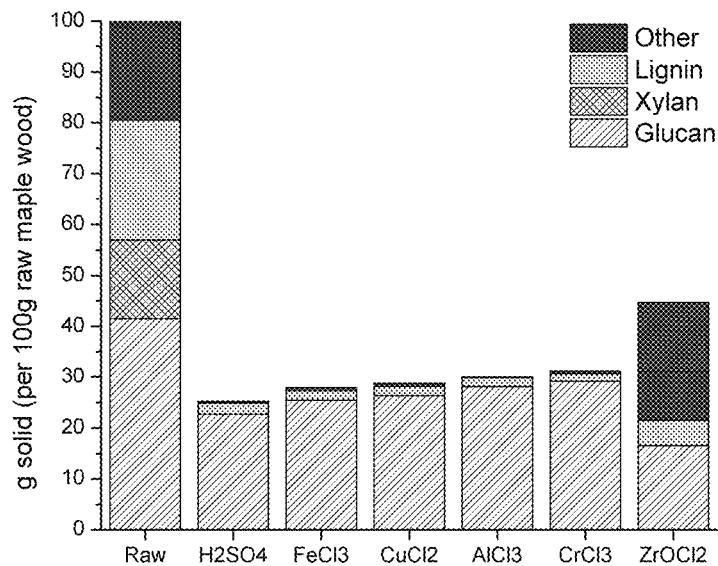
FIG. 11 shows composition of raw maple wood and distribution of major components to the solids remaining after reaction with 1:1 THF co-solvent and various acid catalysts based on 100 g of initial maple wood fed to the systems. Metal halides improved upon sulfuric acid performance by delivering greater amounts of glucan-rich solids for enzymatic conversion to glucose or thermochemical reaction to glucose, 5-HMF, and/or LA. Reaction conditions: 5 wt % maple wood, 0.1M acid catalyst concentration, 1:1 THF:water, 170° C., 30 min batch reactions.

Sulphuric acid is a low-cost mineral acid that is suitable for use as an acid catalyst in this co-solvent system. Other catalysts include, but are not limited to, mineral acids, organic acids, metal halide acids, and heterogeneous acid catalysts can all be applied in this co-solvent system. For example, $FeCl_3$ is a solid acid catalyst that can be applied to selectively achieve high furfural yields from xylose and high 5-HMF yields from solubilized glucose while minimizing LA formation. Under similar reaction conditions, application of $FeCl_3$ catalyst increases the amount of glucan-rich pretreated material which remains after the reaction as compared to an equivalent mass-loading of $H_2SO_4$. This will allow for more glucose production by enzymatic hydrolysis. Since THF helps to promote the deconstruction and solubilization of lignocellulosic biomass, heterogeneous solid catalysts such as porous membrane resins and zeolites can also be used to promote specific target FPs/RIs or reactions. In 1:1 THF:water conditions, using $FeCl_3$ instead of sulphuric acid, a higher mass yield was obtained of remaining pretreated glucan-rich material (25 wt % of glucan initially present in maple wood for $FeCl_3$ vs. 21 wt % for $H_2SO_4$ as shown in FIG. 11) and equivalent furfural production when compared to the reactions with sulphuric acid (85% of theoretical for $FeCl_3$ vs. 87% of theoretical for $H_2SO_4$, shown in Table 4). Also, lower levulinic acid production (2% of theoretical) and higher 5-HMF production (16%) was observed with $FeCl_3$. A higher overall recovery of these FPs was observed using $FeCl_3$ from the C5 (88% of theoretical) and C6 (99% of theoretical) sugars initially present in maple wood than with sulfuric acid.

By using lower severity conditions (lower temperature, lower reaction time, and/or less acid catalyst), the co-solvent system can be specifically used to target the release of xylose sugars, extraction of acid-insoluble lignin, and improving enzymatic digestibility of the remaining glucan-rich material for efficient glucose production using lower enzyme loadings that typically needed with traditional pretreatment strategies. This variation which maximizes monosaccharide production can then be integrated with downstream chemical and biological conversion routes to produce fuels.

Figure 2B:
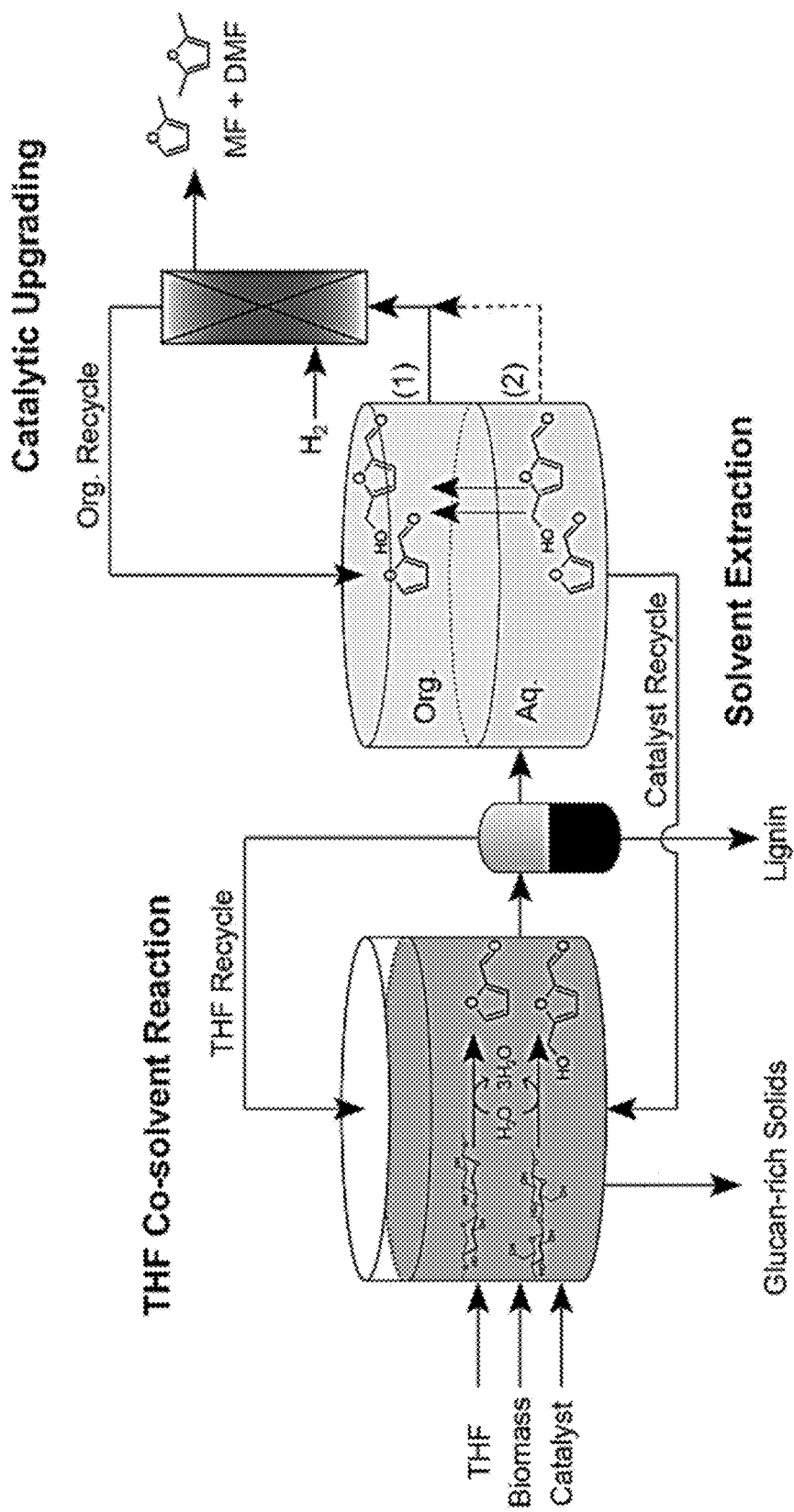
Figure 2C:
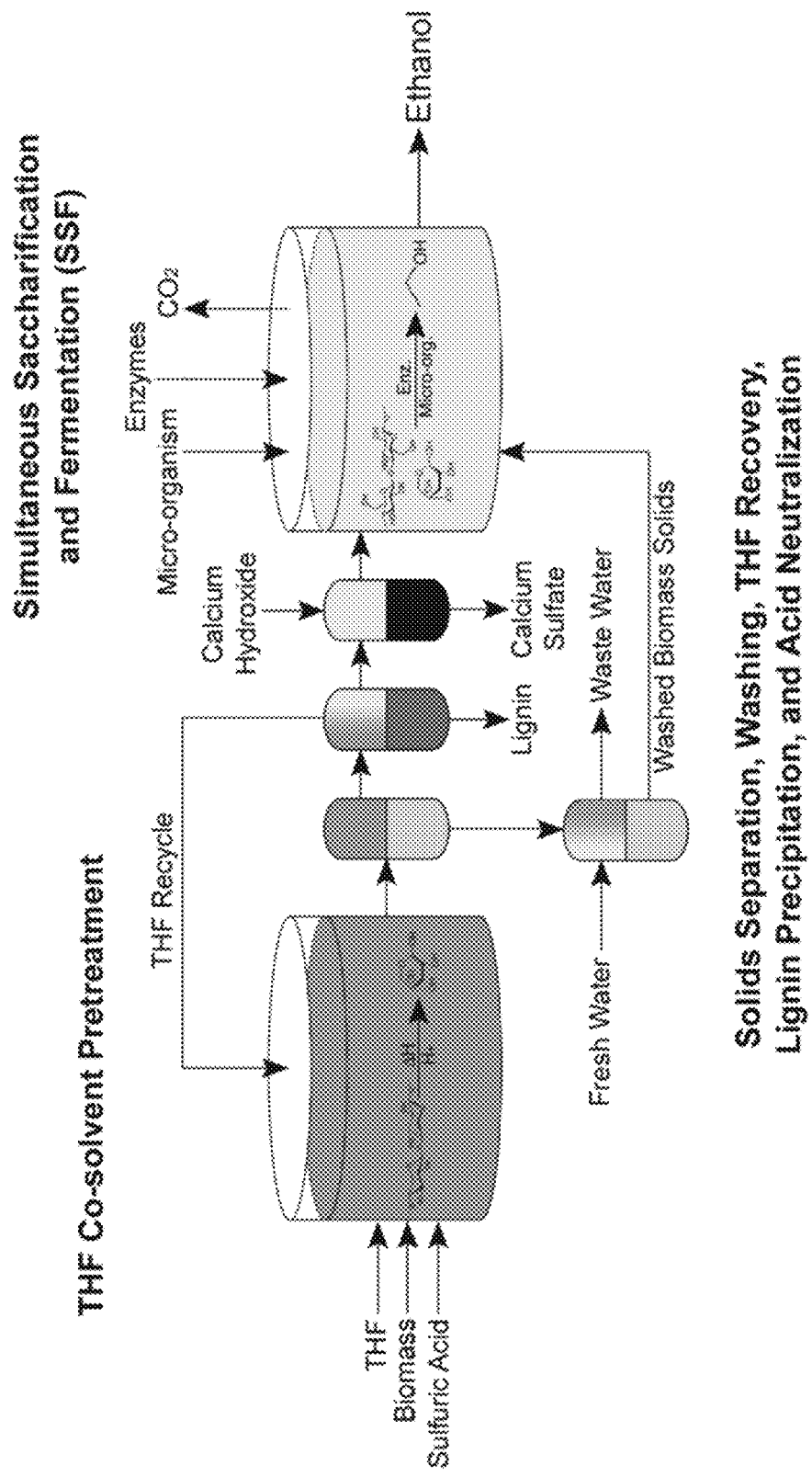
Figure 2D:
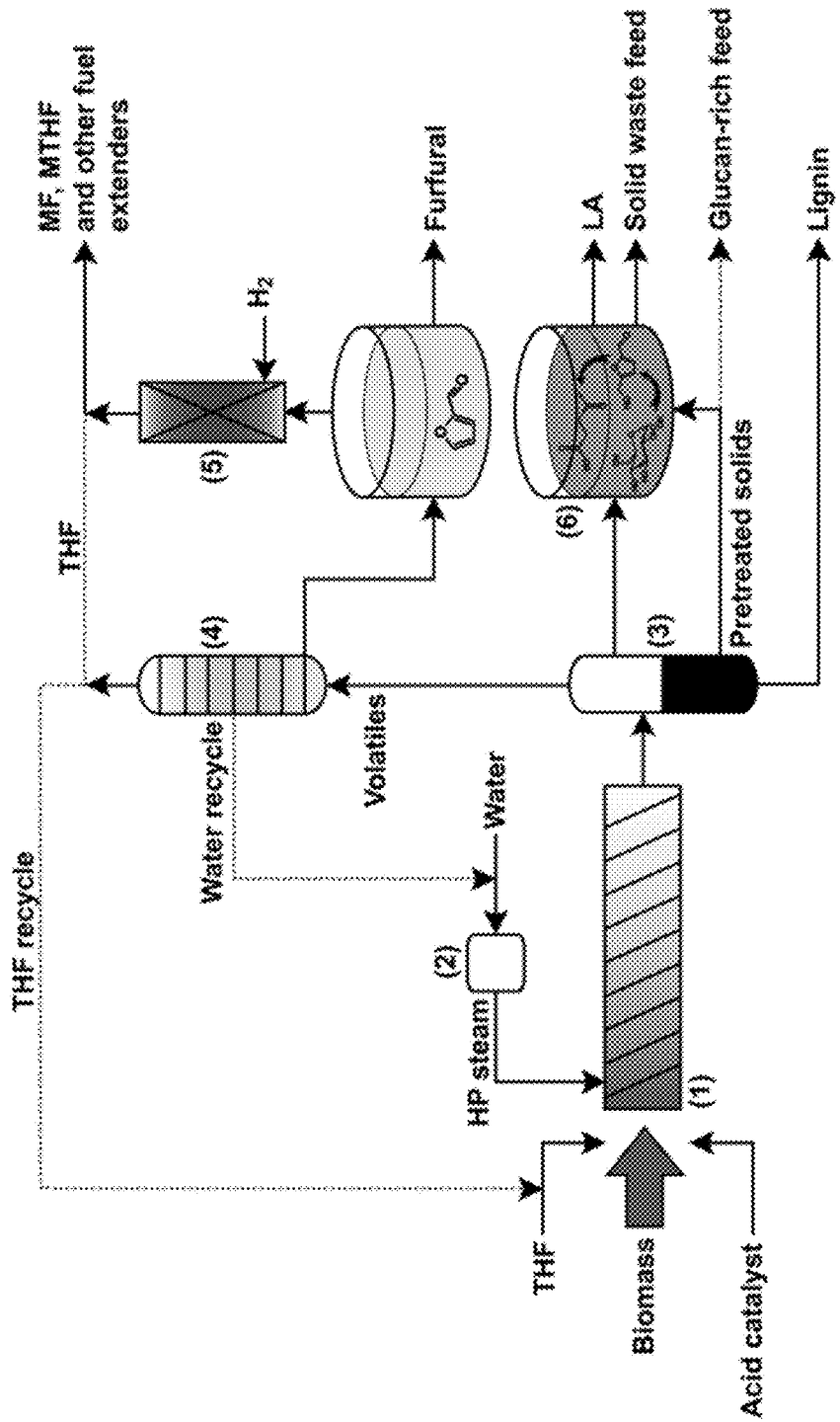

As shown by FIG. 2D, this variation depicts moderately severe reaction conditions in the first stage (150-200° C., 0.5-5 wt % acid catalyst loading) to target the production of furfural from xylose as it is the least stable RI in the catalytically active phase. Thus, by maximizing the recovery of furfural, the overall recovery of FPs can increase. Some 5-HMF will be produced from the hydrolysed hexoses and the remaining glucan-rich solids can be used for glucose production by enzymatic hydrolysis, levulinic acid production in a higher severity second stage reaction (>200° C., >1 wt % acid catalyst loading), or as direct feed for SSF and CBP operations.

In another embodiment, RI production from lignocellulosic biomass is integrated with simultaneous catalytic upgrading of RIs to fuel products such as "drop-in" hydrocarbon fuels and/or gasoline and diesel blendstock. Using moderate to high severity conditions (150-220° C.) and suitable catalysts, furfural and 5-HMF will be first produced and simultaneously recovered for catalytic conversion into drop-in fuels by selective hydrogenation and/or hydrodeoxygenation. The remaining glucose and glucan-rich material will then be subjected to a second high severity reaction (170-250° C.) to produce additional 5-HMF and/or LA for the direct catalytic conversion into drop-in fuels also by selective hydrogenation and/or hydrodeoxygenation. As shown in FIG. 2D, simultaneous catalytic upgrading of FPs in both stages can occur either in the vapor phase above the reaction at each stage (FIG. 2D), or directly in the liquid phase where sugar dehydration reactions are also taking place. If the final fuel products produced by catalytic upgrading at each stage are more stable than the FPs they were produced from, they can be returned to the reaction vessel for final recovery at the end of the second stage reaction as shown in FIG. 2D. The purpose of a two-stage reaction is to maximize the yields of stable fuel products from furfural in the first stage before the production of fuel products from LA and/or 5-HMF in the second stage. Lignin will be extracted and recovered following furfural production.

In one embodiment, the cellulosic material is herbaceous material. In another embodiment, the cellulosic material is agricultural residue. In another embodiment, the cellulosic material is forestry residue. In another embodiment, the cellulosic material is municipal solid waste. In another embodiment, the cellulosic material is waste paper. In another embodiment, the cellulosic material is pulp and paper mill residue.

In another embodiment, the cellulosic material is corn stover. In another embodiment, the cellulosic material is corn fiber. In another embodiment, the cellulosic material is corn cob. In another embodiment, the cellulosic material is orange peel. In another embodiment, the cellulosic material is rice straw. In another embodiment, the cellulosic material is wheat straw. In another embodiment, the cellulosic material is switch grass. In another embodiment, the cellulosic material is miscanthus. In another embodiment, the cellulosic material is bagasse.

The following examples are meant to further illustrate, but not limit the foregoing disclosure or the appended claims.

EXAMPLES

Example 1

The acid-catalyzed reactions of maple wood, D-xylose, and furfural in this disclosure were carried out in solvent and non-solvent water solutions. For most of the reactions, the solvent solution consisted of a 50 vol % (1:1) mixture of THF (>99% purity, Fisher Scientific, Pittsburgh, PA) and deionized (DI) water. Concentrated sulfuric acid (72 wt %, Ricca Chemical Company) was added to the solution to make a 1 wt % acid solution (approx. 0.1M). For the non-solvent control experiments, only DI water was used to prepare the 1 wt % sulfuric acid solution. The reactions were then carried out in a high-pressure continuously stirred 1 L Parr reactor (Parr Instrument Company). The reactor temperature was directly measured by an in-line thermocouple (Omega, K-type). All reactions were maintained at 170° C. (443 K) by convective heating from a fluidized sand bath (Techne, Princeton, NJ) set at 340° C. (613 K) to reduce heat-up time. A PID controller regulated the sand bath temperature. Mixing was performed by twin 6-blade impellers operating at 200 rpm by a top mounted electric motor. The reaction temperature was stabilized by using a mechanical winch to control the height of the reactor over the sand bath. At the conclusion of a run, the reactor was cooled by quickly lowering it into a large room temperature water bath next to the sand bath. Start time was defined as when the temperature first reached 170° C., and final reaction time was recorded when the reactor first touched the cooling water bath. All liquid containing receptacles used were made of glass to prevent the loss of furfural and THF that was observed when plastics were used for the experiments.

Maple wood reactions were carried out using air-dried (<5% moisture content) maple wood chips obtained in upper New York by Mascoma Corporation (Lebanon, NH). The chips were milled and sieved down to 1 mm particle size. The dried and milled samples were then stored at room temperature in gallon-sized Ziploc® bags that were hand-pressed to remove excess air. Maple wood composition was measured according to the established National Renewable Energy Laboratory (NREL) procedure (version 8-03-2012) in triplicates with the result: 40.9±0.3 wt. % glucan, 15.5±0.2% xylan, 2.1±0.1% mannan, 24.4±0.3% K-lignin, and 17.1% other material. The latter was not further characterized in this study but is expected to be made up of ash, sugar acids, and protein. Because arabinan and galactan were not present in significant quantities (<0.3%), it may be appropriate to consider that all maple wood pentosans are xylan and all hexosans are only glucan and mannan. For each run, 40 g (dry wt.) of maple wood and 760 g of solvent or non-solvent acid solution were first transferred to a sealed glass bottle to pre-soak overnight at 4° C. Contents were then equilibrated to room temperature prior to reaction. After each reaction, 1 ml of the liquor was withdrawn, centrifuged, and analyzed by HPLC (Agilent 1200 system equipped with a Bio-Rad Aminex® HPX-87H column and RI detector) with a eluent (5 mM sulfuric acid) flow rate of 0.6 ml/min. Since the HPX-87H column cannot distinguish between xylose, mannose, and galactose sugars, the HPLC was also equipped with an Aminex® HPX-87P column for later analysis of neutralized reaction samples to study the disappearance of xylose. The solids were then separated from the room temperature reaction liquor by vacuum filtration through glass fiber filter paper (Fisher Scientific, Pittsburgh, PA). Mass and density of the liquid fraction were measured to complete accurate yield calculations below. For the solid fraction, mass, moisture content, and composition were measured. Only runs with an overall mass balance of 100±5% were reported. Due to the difference in density between the solvent and non-solvent solutions, densities were determined by weighing 25 ml of the liquid in a volumetric flask after each reaction for yield calculations. Calculation of the RI yields is given by Equation (1) where the molar equivalents ($\theta_{RI}$) of furfural (Eq. 2), LA (Eq. 3), and HMF (Eq. 4) are individually calculated for their respective sugar sources.

$$\% \ RI \ yield = \theta_{RI} * \frac{RI_{prod.}(g/L) * \text{mass of liquor}_{prod.}(g)}{\text{maple wood}_{init.}(g) * \text{density of liquor}_{prod.}(g/L)} * 100\% \quad (1)$$

$$\theta_{furfural} = \frac{1.375}{\text{fraction of total xylan}_{init.}} \quad (2)$$

$$\theta_{LA} = \frac{1.396}{\text{fraction of total hexosan}^a_{init.}} \quad (3)$$

$$\theta_{HMF} = \frac{1.286}{\text{fraction of total hexosan}^a_{init.}} \quad (4)$$

$^a$Total hexosan = glucan + mannan

For the xylose dehydration studies, 10 g of D-xylose (99% purity, Sigma-Aldrich, St. Louis, MO) was transferred to a 1 L volumetric flask and dissolved with either the THF solvent or non-solvent acid solution to achieve a 10 g $L^{-1}$ concentration. A 10 g $L^{-1}$ xylose concentration was equivalent to the effective amount of xylose that would be hydrolyzed from a 40 g sample of biomass with a xylan content of 17.5% (average of 14-21% typically found in biomass). In this way, the calculated rate constants and selectivities would be relevant to the current and future findings. A first-order approximation of xylose dehydration is represented by Equation (5)

$$\text{Xylose} \xrightarrow{k_1} D \quad (5)$$

where D represents the dehydration products. The expression for the rate of xylose (X) disappearance and calculation of the rate constant are given in Equations (6), (7), and (8). Since acid concentration (A) was held constant throughout the studies, it was combined into the overall rate constant k.

$$\frac{d(X)}{dt} = -(k_1 A)X = -kX (1^{st} \text{ order rate law with lumped acid term}) \quad (6)$$

$$\int_{X_{init.}}^{X} \frac{d(X)}{X} = -k \int_0^t dT \quad (7)$$

$$\ln\left(\frac{X}{X_{init.}}\right) = -kt \quad (8)$$

where k will be determined by linear fitting of Equation (8). Results after 30 min were not used in the linear fitting as the xylose solution became too dilute for accurate quantification. Because not all dehydration products are furfural, determination of the furfural yield for each reaction was used to calculate the furfural selectivity by Equation (9):

$$\% \text{ Furfural selectivity} = \frac{\% \text{ mol furfural yield}}{\% \text{ xylose converted}} * 100\% \quad (9)$$

A total 800 g of xylose solution was used for each reaction in a 1 L Parr reactor, and analysis was performed by HPLC. Similarly, for the furfural decomposition studies, reactions were performed with 6.4 g $L^{-1}$ of furfural (99% purity, Sigma-Aldrich, St. Louis, MO) in THF solvent and non-solvent acid solutions in a 1 L Parr reactor. Since 6.4 g $L^{-1}$ is the molar equivalent of 10 g $L^{-1}$ xylose at 100% conversion, these reactions provide insight to the amount of furfural lost by self-resinification in comparison to furfural loss by condensation reactions in the presence of xylose.

Two glass bottles each with 5 wt % maple wood were used. One contained a 1:1 ratio of THF to water and the other an aqueous solution with no solvent. Aside from the pigmentation from the maple wood in the solvent solution, the two media were nearly identical. The contents of these bottles were then transferred to a Parr reactor and reacted at 170° C. A reaction temperature of 170° C. was determined to be useful for studying the production of furfural in the presence of a solvent. As raw biomass often contains significant moisture content (up to ~50 wt % in woods), an appropriate ratio of solvent to total water must be selected to minimize thermal loads and maximize solids loading. Since emphasis is placed on the direct conversion of raw cellulosic biomass, a 1:1 or less solvent to water ratio is desirable in this case to minimize the use of the solvent and maximize thermal efficiency.

TABLE 1

Acid-catalyzed production of furfural, LA, and HMF from maple wood and D-xylose in batch reactions with and without THF added$^a$

| Run # | Solvent content$^d$ | Substrate | $H_2SO_4$ (wt %) | Time (min) | Temperature (° C.) | Yields | | |
|---|---|---|---|---|---|---|---|---|
| | | | | | | Furfural (mol %) | HMF (mol %) | LA (mol %) |
| 1 | None$^f$ | Maple wood$^b$ | 1 | 40 | 170 | 62 | 2.4 | 7.2 |
| 2 | 1:3 THF:Water | Maple wood$^b$ | 1 | 40 | 170 | 76 | 4.9 | 8.3 |
| 3$^e$ | 1:1 THF:Water | Maple wood$^b$ | 1 | 40 | 170 | 87.0 ± 1.4 | 12.7 ± 0.4 | 10.8 ± 0.1 |
| 4 | 3:1 THF:Water | Maple wood$^b$ | 1 | 40 | 170 | 87 | 20 | 29 |
| 5 | None$^f$ | Maple wood$^b$ | 1 | 120 | 170 | 39 | 2.6 | 32 |

TABLE 1-continued

Acid-catalyzed production of furfural, LA, and HMF from maple wood
and D-xylose in batch reactions with and without THF added[a]

| | | | | | | Yields | | |
|---|---|---|---|---|---|---|---|---|
| Run # | Solvent content[d] | Substrate | $H_2SO_4$ (wt %) | Time (min) | Temperature (° C.) | Furfural (mol %) | HMF (mol %) | LA (mol %) |
| 6 | 1:1 THF:Water | Maple wood[b] | 1 | 120 | 170 | 69 | 7.6 | 40 |
| 7 | None[f] | Xylose[c] | 1 | 40 | 170 | 60 | — | — |
| 8 | 1:1 THF:Water | Xylose[c] | 1 | 50 | 170 | 73 | — | — |
| 9[g] | None | Maple wood[h] | 1.5 | 40 | 200 | — | — | 75 |

[a]All reactions were performed using a 1 L Parr reactor and reported yields are % of theoretical maximum.
[b]5 wt % solids loading.
[c]10 g $L^{-1}$ initial xylose concentration.
[d]The ratio of solvent to water is as described.
[e]Yields were calculated based on an average of three runs with standard deviation shown.
[f]These reactions were control experiments without solvent.
[g]Production of LA from pretreated maple wood after hemicellulose extraction.
[h]10 wt % solids loading Table 1 compares yield data for furfural, LA, and HMF production from maple wood and D-xylose between THF co-solvent and non-solvent reactions. Runs 2 to 4 in Table 1 compare the highest furfural, LA, and HMF yields obtained from maple wood reactions using 1:3, 1:1, and 3:1 volume ratios of THF and water respectively. Lower RI yields overall were observed in the 1:3 mixture, identical yields of furfural were achieved with 1:1 and 3:1 solutions, and the highest yields of LA and HMF were obtained from the 3:1 mixture. Although higher solvent ratios may result in marginal yield benefits, additional solvent recovery costs, increased heating requirements, and limited solids loading are likely to be detrimental to process economics. For these reasons, a 1:1 solvent ratio was chosen for further investigation. Runs 1 and 3 compare the non-solvent and THF reactions at 40 min when furfural yield was highest. Runs 5 and 6 compare the non-solvent and THF reactions at 120 min when there was greater LA production. Under identical process conditions, the presence of THF co-solvent significantly improved the yields of furfural (~25 mol % improvement) and HMF (~10 mol %) at 40 min, and levulinic acid (~8 mol %) yields at 120 min as compared to the non-solvent case.

HMF is an important platform chemical that is first produced from the acid catalyzed dehydration of hexoses. When HMF is allowed to remain in the catalytically-active aqueous phase, it will readily hydrolyze to form equimolar amounts of LA and formic acid (FA). Since LA is more stable than HMF in an aqueous environment, higher final yields of LA were observed in single phase reactions. The application of solid acid catalysts have been shown to improve HMF selectivity when using THF. The highest yield of furfural, the primary RI targeted in this study, was 87 mol % of theoretical at 40 min in both the 1:1 and 3:1 THF co-solvent reactions. At this time, LA yields were approximately 11 mol % with 1:1 THF, 29 mol % with 3:1 THF, and 7 mol % without (Table 1). The room temperature liquid densities after the 40 min reactions (0.9987 g $L^{-1}$ with 1:1 THF and 1.0152 g $L^{-1}$ without THF at 21° C.) accounted for a 2% difference in the maximum furfural yield. For both solvent and non-solvent reactions in Table 1, the highest furfural yield was achieved much sooner (40 min) than the highest LA yield (120 min). Due to the more acid labile amorphous structure of hemicellulose, the rate of hydrolysis of xylan from hemicellulose was much greater than that of glucan from crystalline cellulose. By increasing the ratio of THF to 3:1, the co-production yields of furfural and LA improved as more hydrolysis of the hexosans occurred.

Figure 3A:
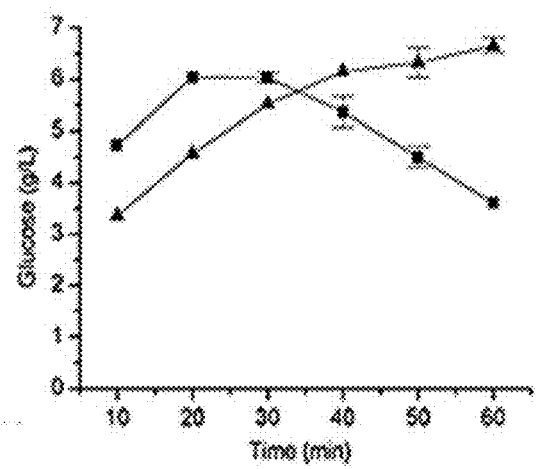
FIG. 3A-E are graphs of concentration profiles of RIs and glucan-rich solids produced from the THF co-solvent reaction at 170° C. Concentration profiles of (A) glucose, (B) xylose+mannose+galactose, (C) LA, and (D) furfural over 60 min of reaction time (■ with THF, ▲ without THF). (E) Composition of raw maple wood and remaining glucan-rich solids after reaction with and without THF co-solvent. THF dissolved over 90% (by wt.) of the lignin and degradation tars that otherwise accumulated in the non-solvent case. Reaction conditions: 5 wt % maple wood and 1 wt % $H_2SO_4$ in batch reactions at 170° C. The THF co-solvent solution contained a 1:1 ratio of THF and DI water.

FIG. 2A-D compares the concentration profiles of the RIs produced from the maple wood reactions with and without THF as a co-solvent over 60 min of reaction. As shown, the higher initial concentration of glucose (10 min) in the THF reaction suggested that THF helped to enhance the hydrolysis of cellulose to release glucose much sooner than the non-solvent case. By 20 min, the concentration of glucose in the THF reaction had started to decrease and the formation of LA and consumption of glucose became significantly greater than the non-solvent case. As discussed above, the column first used could not differentiate xylose, mannose, and galactose monomers by their retention times so a lumped concentration profile is shown. Due to the much slower decomposition rate of mannose over xylose, the exact concentration profile of xylose could not be determined. Instead, xylose concentration was measured from neutralized reaction samples separately and found that xylose had been completely consumed by 40 min in the presence of THF and by 60 min in the non-solvent case (compare with FIG. 3A). These results indicated that THF had a catalytic effect on the destruction of both glucose and xylose.

Figure 3B:
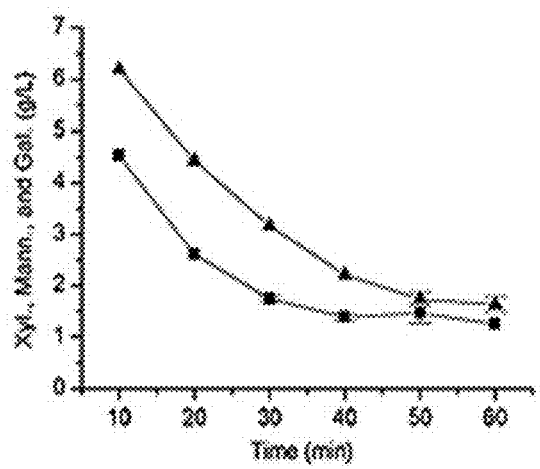
Figure 3C:
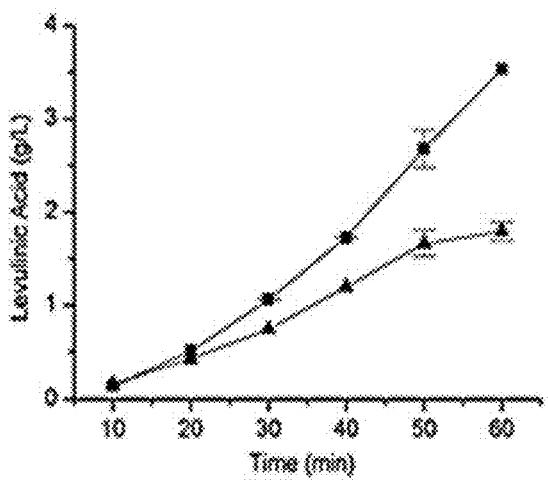
Figure 3D:
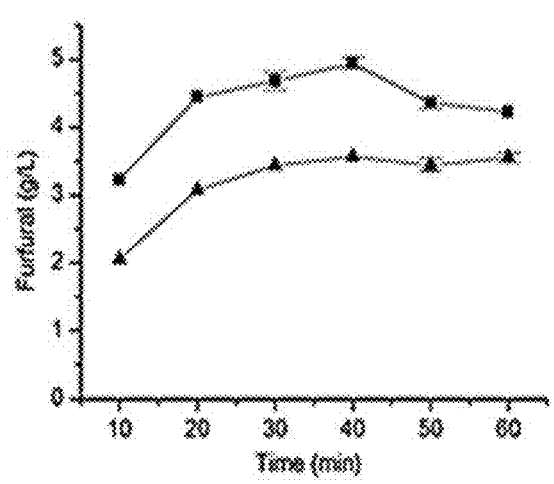

After 120 min of reaction, there was still some glucose remaining (<1 g $L^{-1}$). By then, the yield of furfural had decreased to 69% (21% loss relative to the highest furfural observed at 40 min) with THF and 39% without (37% loss relative to the highest furfural observed at 40 min). This was the first evidence that THF helped reduce furfural loss in the catalytically-active aqueous phase. However, effective co-production of these RIs was still limited by rapid degradation of furfural. Furfural losses can be attributed to condensation reactions between furfural and intermediate sugar products, the slow conversion of furfural to formic acid, and the formation furfural resins and other degradation products. Because furfural concentrations decreased sharply after 40 min in the presence of THF (FIG. 3D), allowing the reaction to continue further will hurt yields. Thus, in order to maximize utilization of all cellulosic sugars, optimization of the least stable species is paramount, and separate steps to independently target production of furfural and levulinic acid will be necessary to achieve the highest total yield of the two combined.

Figure 3E:
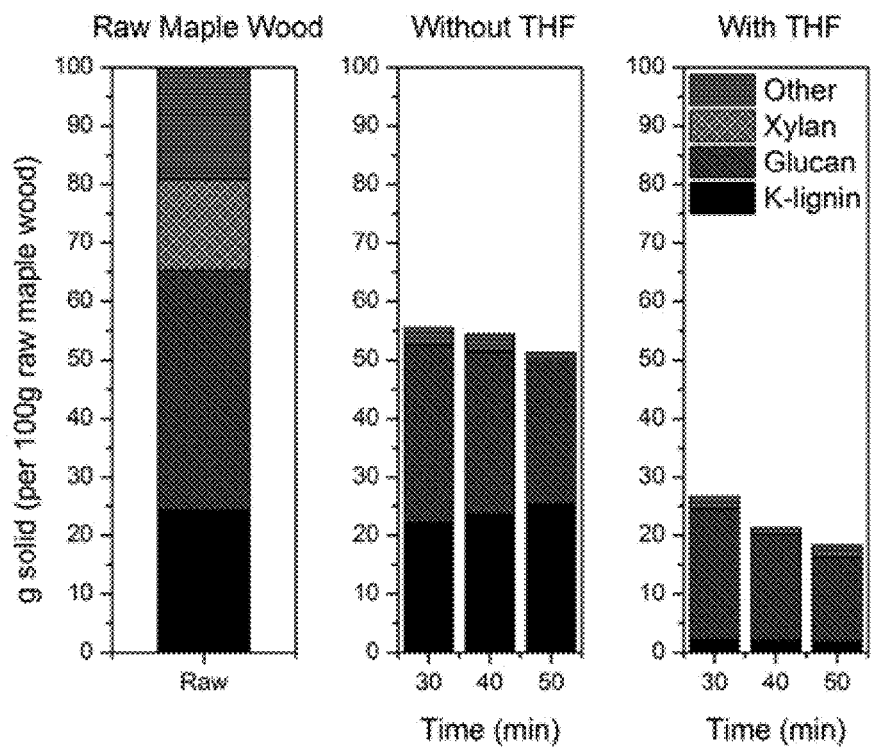

FIG. 3E shows the composition of the remaining solid fraction after reactions with and without THF on the basis of 100 g of raw maple wood. Unique to the THF co-solvent reactions was the nearly complete removal of acid-insoluble lignin and degradation tars that accumulate with the non-solvent reactions. Over 90% (by wt.) of the insoluble lignin was removed by THF and the amount of insolubles remaining in the solid fraction was minimal throughout the reaction (FIG. 3E). Without THF, insoluble lignin was initially reduced, but the formation of insoluble tars and degradation products increased over the course of the reaction. Upon vacuum filtration of the reaction liquor, the unreacted solids in the THF reactions were almost exclusively composed of glucan (85 wt % at 40 min, FIG. 3E). In effect, the THF system behaved similar to an organosolv process. Due to the nearly complete removal of inhibitory hemicellulose and lignin fractions, these pretreated solids should be readily accessible to enzymatic attack and serve as an ideal feed for enzymatic hydrolysis into fermentable glucose. The higher initial glucose concentrations in the THF reactions (FIG. 3A) suggest improved digestibility of the pretreated solids. Although reactions using $H_2SO_4$ have been demonstrated by optimizing the reaction conditions and the type of acid catalyst used in the solvent reactions, the amount of unhydrolyzed glucan-rich solid residue can be increased to favor production of fermentable glucose. The washed solids could thus be a potential feed for SSF or CB operations or targeted for levulinic acid production.

After reaction, THF was recovered by vacuum distillation of the filtered liquor at room temperature to produce a dark-brown sticky precipitate from the liquid phase that stuck to the walls of the glass bottle. This residue contained extracted lignin and degradation products that had been dissolved in the co-solvent solution. The now concentrated aqueous acid solution was then poured out, and the solid lignin precipitate was collected and washed with diethyl ether to produce the dark-brown powdered lignin product. The lignin residue could then be redissolved by a suitable organic solvent to be catalytically upgraded. The applications of lignin for conversion into fuel products and valuable polymers are discussed elsewhere.

TABLE 2

First-order rate constants for the disappearance of D-xylose with and without THF and comparisons to previous literature[a]

| Rate Constant | With THF (A/min) | Without THF (A/min) | Literature (A/min) |
|---|---|---|---|
| $k^b$ | 0.109 ± 0.015 | 0.0557 ± 0.0018 | 0.0527[c] |

[a]Reaction conditions: 10 g L-1 D-xylose and 1 wt % H2SO4 in batch reactions at 170° C. THF co-solvent solution contained 1:1 THF and DI water.
[b]Rate constant includes a 0.204 M hydrogen ion (A) term.
[c]Calculated from Eq. (1) on pg. 16 given by K.J. Zeitsch (2000)[15]

Figure 4A:
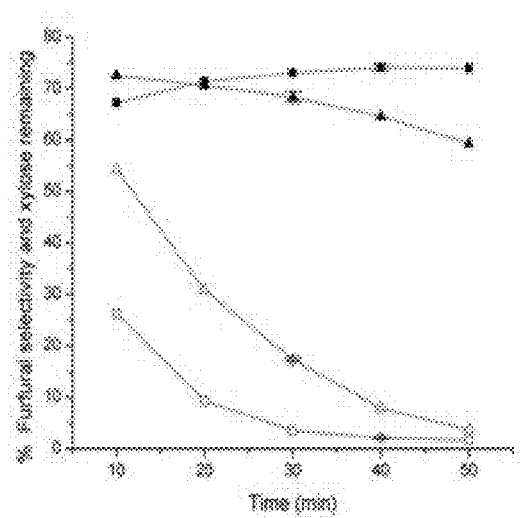
FIG. 4A-B shows the ability of the THF co-solvent reaction to improve furfural selectivity from xylose and protect furfural from degradation. (A) Selectivity of furfural in reactions from 10 g $L_{-1}$ pure D-xylose (■ with THF, ▲ without THF) and remaining xylose in solution (□ with THF, △ without THF). (B) Furfural remaining (%) for reactions from 6.5 g $L^{-1}$ pure furfural (■ with THF, ▲ without THF).

In addition to applications to maple wood, acid-catalyzed dehydration reactions with pure D-xylose were also performed to determine the specific effects that THF had on the xylose disappearance rate as shown in Table 2 and furfural selectivity as shown in FIG. 4A. Reactions were performed with 10 g $L^{-1}$ xylose solutions under the same conditions as the maple wood reactions to study xylose conversion to furfural without interference from other biomass components. The amounts of xylose remaining from the solvent and non-solvent reactions are also shown in FIG. 4A. The rate constants reported in Table 2 were then determined by a linear fit of a first-order rate expression. To assure that the reaction system was not mass transfer limited and represented the actual kinetics, the rate constant from the non-solvent control reactions was compared to a calculated result from an empirical model reported in previous literature, also shown in Table 2, and found to be very close. The results demonstrated that THF had greatly (~2 times) improved the rate of xylose disappearance, which suggested that the presence of THF had a catalytic effect on xylose dehydration.

Because not all of the dehydration products were furfural, Equation (9) was employed to calculate the furfural selectivity for these reactions. For non-solvent reactions, furfural selectivity was initially higher (72% at 10 min) (FIG. 4A), but as the reaction proceeded, selectivity to furfural decreased dramatically to only 59% by 50 min. As more furfural was produced, the formation of irreversible byproducts increased. For the reactions with THF, furfural selectivity was initially lower (67% at 10 min) but continued to increase over the course of the reaction, surpassing the non-solvent selectivity at 20 min to reach a maximum of 74% by 40 min. Although the exact reason for these differences is not yet clear, the lower initial furfural selectivity for the solvent reactions may be due to the increased dehydration rate of xylose resulting in competing xylose intermediates. Subsequently, as xylose was more rapidly consumed in THF, furfural selectivity increased as the opportunity for condensation reactions with the intermediate products was reduced. In any event, the overall reduced formation of byproducts in the presence of THF resulted in a higher maximum furfural yield from xylose of 73 mol % with THF compared to the 60 mol % yield from the non-solvent system (Table 1). However, when compared to the maple wood reactions, the furfural yields from pure xylose were lower, especially for the solvent case. This phenomenon was also observed with milled poplar wood chips. Higher initial xylose concentrations in the pure xylose reactions could increase the degree of cross-polymerization with furfural early on while the slower release of xylose from maple wood may reduce this effect.

Figure 4B:
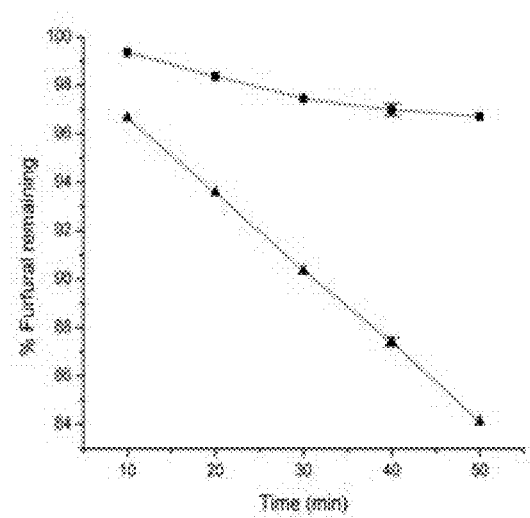
Figure 5:
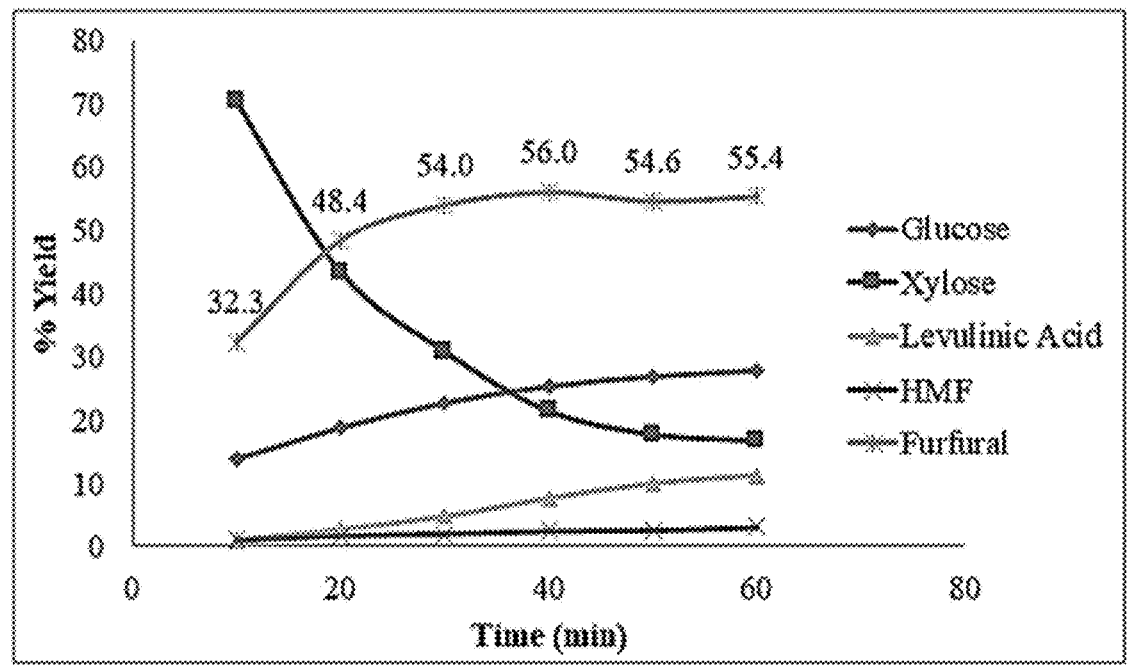
FIG. 5 is a graph of product yields from raw maple wood reactions in a 1 L Parr® reactor at 170° C. and 1% (w/w) $H_2SO_4$ solution in water only. Numbered labels represent the furfural yield at each reaction time.
Figure 6:
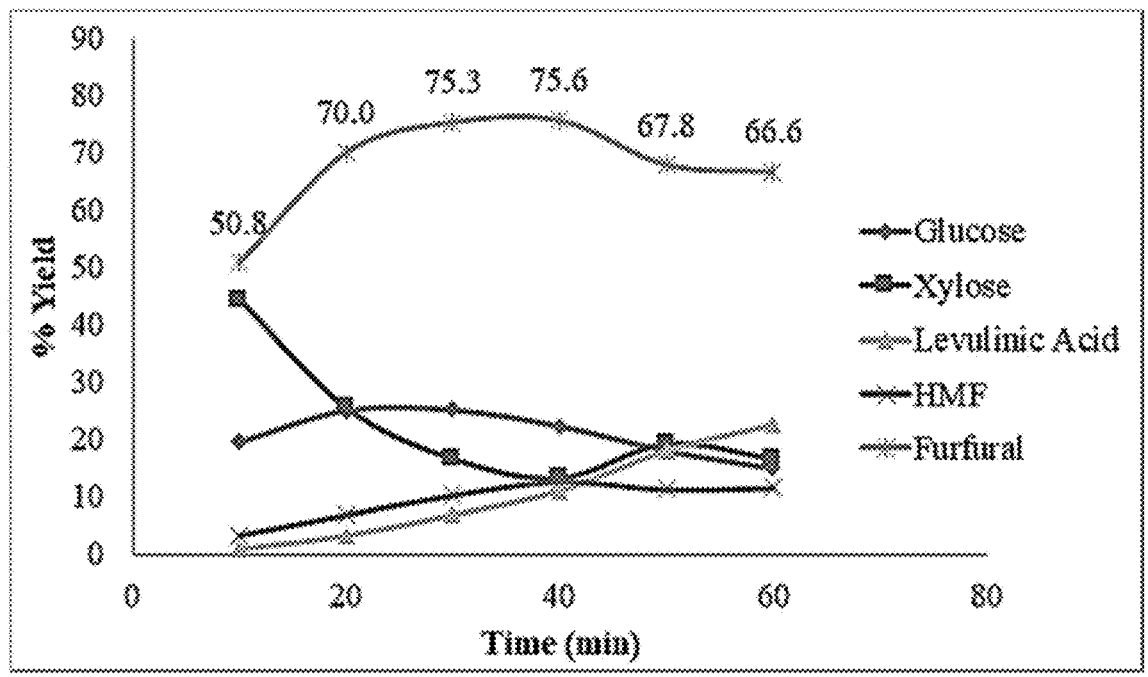
FIG. 6 is a graph of product yields from raw maple wood reactions in a 1 L Parr® reactor at 170° C. and 1% (w/w) $H_2SO_4$ in a 1:3 (v/v) solvent solution of tetrahydrofuran and water. Numbered labels represent the furfural yield at each reaction time. As shown, the presence of THF in the solution mixture allows for the improvement of furfural yields in the reaction by up to 20%. Levulinic acid yields were also improved over the water only reactions by over 11% at 60 min of reaction (reaction temperature was optimum for furfural production).
Figure 7:
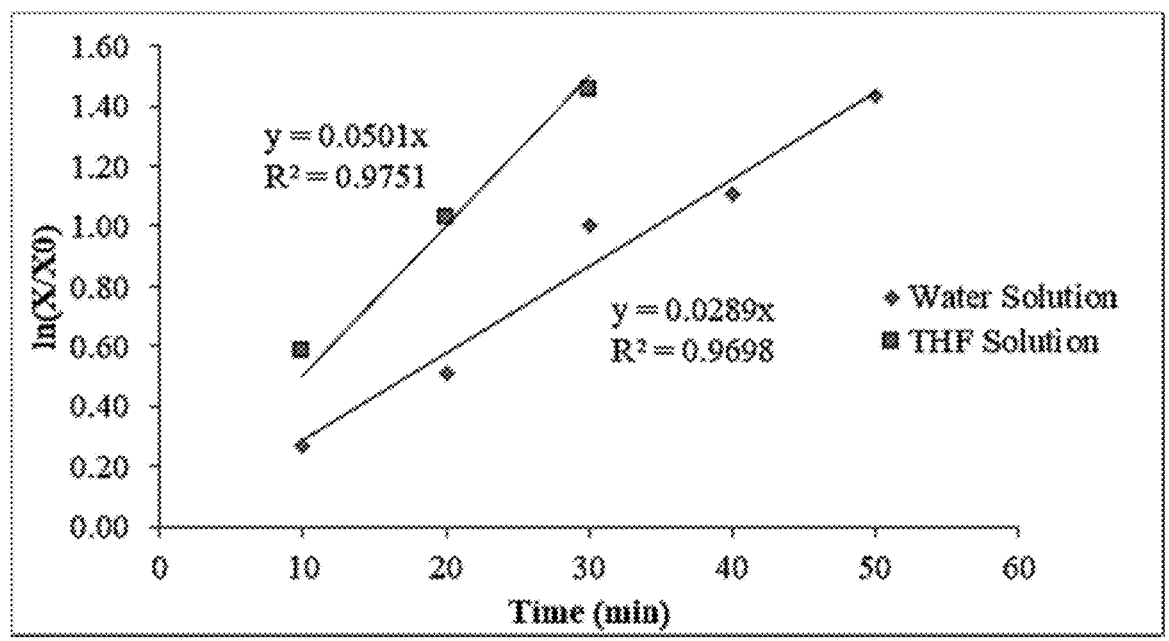
FIG. 7 is an initial plot comparing the calculated rate constants between a water solution and a THF solvent solution of pure xylose and 1% (w/w) $H_2SO_4$. Reactions were performed using a 1 L Parr® reactor at 170° C. The THF solution is composed of a 50% (v/v) solvent mixture of tetrahydrofuran and water. Initial xylose (XO) concentration was 10 g/L. Labels represent a linear regression of the normalized xylose conversion data and the k value of the reaction is represented by the slope and expressed in units of [$min^{-1}$]. As shown, the rate of xylose conversion is much faster in the THF solvent solution than in just water.
Figure 8:
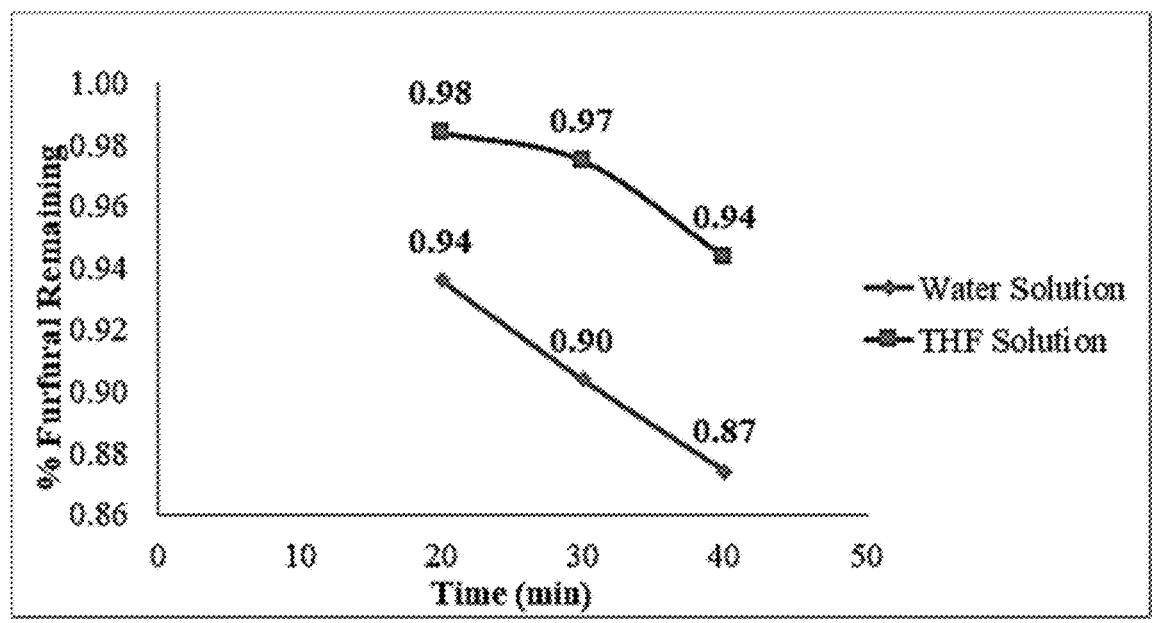
FIG. 8 is a plot of a single experiment comparing the degradation profile of furfural between a water solution and a THF solvent solution of furfural and 1% (w/w) $H_2SO_4$. Reactions were performed using a 1 L Parr® reactor at 170° C. As shown, the THF solvent solution helps to prevent as much as 7% of the furfural present in solution from degradation.
Figure 9:
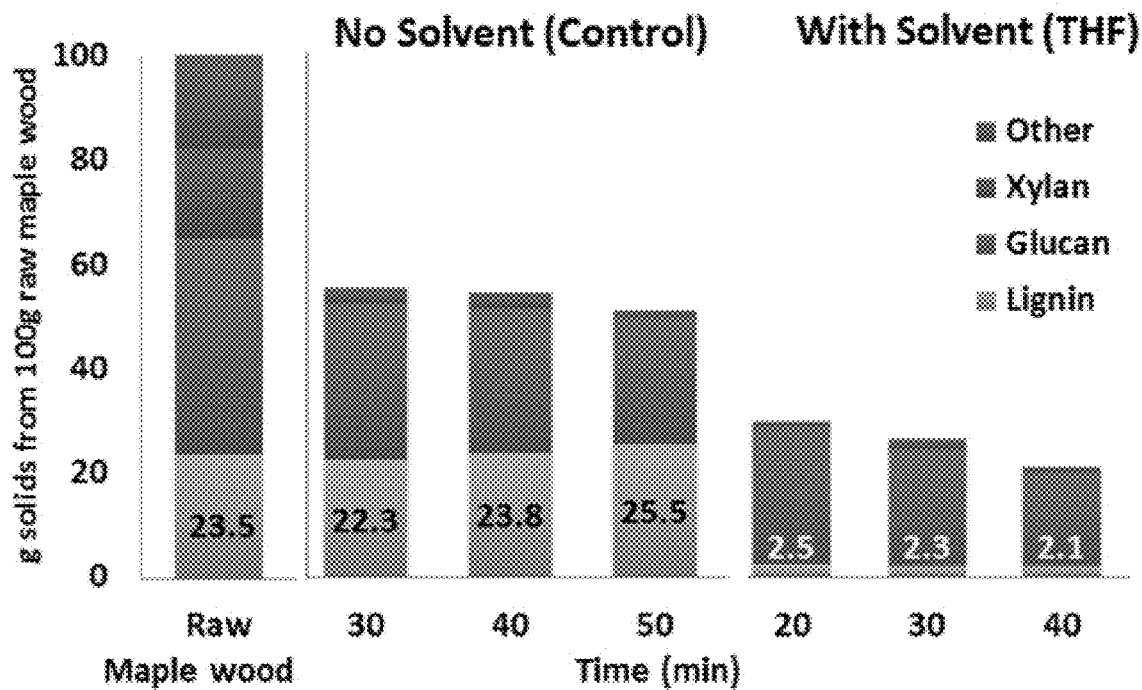
FIG. 9 depicts a comparison of the maple wood composition of the remaining solid fraction over time after an acid catalyzed reaction in 1 L Parr® reactor at 170° C. between a THF solvent solution and a water solution. Comparison of reacted samples is made based on the composition of 100 g of unreacted raw maple wood. As shown, up to 90% of the insoluble lignin and tars can be removed in the reactions with THF. Without the solvent, the insoluble fraction of lignin and tars increases over time.

FIG. 4B shows the degradation of 6.5 g $L^{-1}$ pure furfural at 170° C. under solvent and non-solvent conditions. After 50 min of reaction, furfural loss was only about 3% with THF in the solution, whereas the non-solvent case saw furfural losses of up to 16%. The 13% difference in furfural loss between the two cases in FIG. 4B accounted for most of the furfural yield difference between the solvent and non-solvent reactions with pure xylose, which shows that THF plays a primary role in preventing furfural loss by resinification. Interestingly, formic acid formation accounted for nearly all the furfural lost in the THF reactions but less than half of the furfural lost in the non-solvent reactions. Although the reaction severities were too mild to effectively study the kinetics of furfural destruction in only 50 min, the data roughly correlated to the proposed first order loss approximation for the non-solvent case, whereas furfural loss in THF did not appear to follow first-order kinetics.

The application of THF as a co-solvent in a biomass conversion process to improve RI yields can be performed by the addition of THF to an acid-catalyzed process. The combined benefits of higher RI yields and complete fractionation of biomass from this solvent system can be achieved at commercial scale by modifying existing continuous furfural technologies with additional separation and recycle processes to collect the pretreated biomass, isolate the lignin fraction for upgrading, and recover the low-boiling solvent. As an example of the possibilities, FIG. 2D shows a simplified conceptual process flow diagram for the integrated production of reactive intermediates and lignin from cellulosic biomass using THF as a co-solvent. Since THF dissolved in the aqueous phase, a higher solids loading can be achieved for greater thermal efficiency compared to a two phase system. Optimization of the highest wt % solids will be determined by the type and moisture content of the raw feedstock and the processing equipment options.

As shown in FIG. 2D, a suitable feedstock, such as milled wood chips, is first soaked in a solution containing THF and an acid catalyst. The slurry is then fed into a screw-type Pandia reactor (1), much like the ones used in the 1960s for continuous furfural production, to keep residence times reasonably uniform to minimize unnecessary byproduct formation. Rapid reactor heat up is provided by high-pressure steam from a boiler (2) to temperatures of around 170° C. or higher, depending on the durability of the vessel. The hot slurry is quickly released at the exit of the Pandia reactor into a separation unit (3) at reduced pressures. In this step, water-volatile components, such as furfural and THF, are flashed or boiled off with steam to distillation (4). The THF azeotrope contains only about 4.6 wt % water so its recovery at this composition is not demanding as additional drying is not necessary. The dotted lines from (4) in FIG. 2D show the recycle streams for both THF and water. HMF, LA, and sulfuric acid are not volatilized with the water and are concentrated with some hydrolyzed glucose in the remaining aqueous layer in (3). For recovery of HMF and LA, solvent extraction or vacuum distillation can be applied to reduce unwanted reactions. However, if only LA production is desired, the concentrated aqueous solution can be sent directly to a continuously stirred reactor (CSTR) (6) for a higher temperature reaction (>200° C.).

From previous observations, the removal of THF from the liquid phase caused lignin to precipitate as a solid residue. Due to its sticky nature, a suitable solvent is likely needed to re-dissolve the extracted lignin for further processing and catalytic upgrading into high value products. In line with this, pure THF readily re-dissolves the recovered lignin. Assuming an efficient continuous device, such as a Hydro-clone®, is available to effectively collect the remaining glucan-rich solid fraction, the solids can be washed, neutralized, and enzymatically hydrolyzed into fermentable glucose or used as processed feed for CBP and SSF operations. In this case, high severity conditions that would be undesirable when xylose and other hemicellulose sugars are targeted can be applied to make furfural. This approach has an added benefit that the combination of high severity reaction conditions with lignin removal should make the resulting solids more easily hydrolyzed with low enzyme doses than has been achieved with other pretreatment systems that are constrained by the need to use low severities to avoid large loses of xylose to furfural when xylose fermentation is targeted. Or, the glucan-rich material can be directly sent to the high temperature CSTR for additional LA production (6), as shown by the solid line (FIG. 2D).

As shown by run 9 in Table 1, LA of up to 75 mol % yield of theoretical could be obtained from cellulose enriched maple wood after the extraction of hemicellulose by hydrothermal pretreatment. The production of LA in this case was obtained from a 200° C. batch reaction with a higher solids loading (10 wt %) more concentrated sulfuric acid (1.5 wt %) and without using any solvent. These results demonstrated that high yields of LA can be obtained from the hemicellulose-free glucan-rich material which remains from the THF reactions if reaction temperatures were increased to specifically target LA production.

The purified furfural product can be sold as is or decarbonylated and hydrogenated to make additional THF. Hydrogenation remains the most versatile option to upgrade furfural and levulinic acid to fuel products, but the source and cost of hydrogen for catalytic upgrading of these RIs must be carefully considered. Furfural can be upgraded to furfuryl alcohol (FFA), tetrahydrofurfuryl alcohol, and dihydropyran. Methylfuran and methyltetrahydrofuran are hydrogenated products of FFA which can directly serve as gasoline additives. Aldol condensation and dimerization of furfural followed by hydrodeoxygenation can produce alkanes up to tridecanes. The diversity of potential products from furfural greatly improves its marketability at the high yields obtained from this process. Since LA is more stable than HMF in aqueous solution, it is an important primary product from cellulose in this process that can be a valuable chemical precursor to levulinate esters, GVL, MTHF, and other potential fuel products by hydrogenation. LA's high boiling point (245° C.) makes it difficult to separate by distillation without applying a vacuum, so maintaining a concentrated LA product stream will improve separation economics and allow for solvent extraction. Since the production of LA benefits from more severe reaction conditions, a two-stage production strategy for both furfural and LA will achieve the highest RI yields from biomass.

Although most of the THF was recovered, some THF was lost to acid-catalyzed ring-opening reactions. Thus, reducing the reaction time should reduce THF loses. Fortunately, THF itself is a versatile chemical that has commercial application as a solvent for the manufacture of plastics and is closely related to 1,4-butanediol (BDO) and γ-butyrolactone (GBL). Since THF polymers (PolyTHF and PTMEG) are also major commercial products, further investigation into the application of these products will be of great interest, particularly for the potential production of THF from furfural.

To investigate the possibility of furfural production from glucose in the system, 18.7 g $L^{-1}$ glucose solution containing THF and 1 wt % sulfuric acid was reacted at 170° C. After 40 min of reaction, trace amounts of a substance was found that eluted at the same time as furfural (approx. 44 min) on the Aminex® HPX-87H column, however, was not present in the non-solvent reactions. Since certain compounds are known to have similar retention times on this column, additional quantification of this furfural-like compound by GC-MS is needed to confirm its identity. The contribution of this trace compound (0.12 g $L^{-1}$) could account for approximately 2.5% of the measured furfural yield at 40 min from the maple wood reactions. However, since this amount resulted from reaction of pure glucose in the absence of glucan hydrolysis, it provides an upper limit to the possible enhancement in furfural yields reported in this paper. Furthermore, in glucose reactions with THF, a more significant quantity (0.97 g $L^{-1}$) of another glucose-derived compound was measured at the same elution time as xylose (approximately 9.7 min). This non-xylose saccharide (or some other unidentified compound) could explain why similar minute concentrations in FIG. 3B were still observed in the maple wood reactions after 40 min when xylose had been completely consumed. The persistence of this compound and the very minor production of furfural from glucose suggested that an alternate glucose intermediate was the culprit.

The disclosure demonstrates the application of THF as a single-phase co-solvent for significantly enhancing yields of RIs from aqueous processing of lignocellulosic biomass, such as maple wood or corn stover. For the first time, the disclosure shows that a single phase solution of THF and water can (1) improve hydrolysis of hemicellulosic and cellulosic polysaccharides; (2) help catalyze dehydration of the resulting monomeric sugars into FF, hydroxymethylfurfural (HMF), and levulinic acid (LA) at high yields; (3) dissolve the acid-insoluble lignin and degradation products from biomass into the liquid fraction for conversion into high-value byproducts; and (4) generate an easily hydrolysable glucan-rich solid fraction that can be used for enzymatic digestion, fermentation, or further chemical conversion. The targeted production of reactive intermediates from lignocellulosic biomass by an integrated single phase solvent process with THF allows for the effective utilization of all major constituents of lignocellulose, including lignin. The energy-light strategy that is proposed here was designed to complement the most recent advances in catalytic technology, while providing an efficient solution for handling raw feedstock. Increased flexibility in the types of end products allows for continued advancements in improving the deconstruction and catalytic upgrading of lignocellulosic biomass for conversion into renewable fuels and chemicals.

Example 2

Reagent-grade THF (>99% purity, Fisher Scientific, Pittsburgh, PA) was used in all THF co-solvent reactions. The THF co-solvent solution was prepared on a volume basis of increasing the amount of THF additions to realize 1:1 (THF 50% v/v) to 7:1 (THF 87.5% v/v) THF-to-water ratios. Metal halide catalysts were purchased from Sigma Aldrich (St. Louis, MO, US). The hydrate form of each metal halide catalyst ($AlCl_3 \cdot 6H_2O$, $CuCl_2 \cdot 2H_2O$, $CrCl_3 \cdot 6H_2O$, $FeCl_3 \cdot 6H_2O$, and $ZrOCl_2 \cdot 8H_2O$) was used but were loaded based on their equivalent anhydrous mass to achieve 0.1M or 1 wt % catalyst loading. Concentrated sulfuric acid (72 wt % $H_2SO_4$) was purchased from Ricca Chemical Company (Arlington, TX) and used to make dilute sulfuric acid solutions.

Maple wood chips obtained in upper New York State were provided by Mascoma Corporation (Lebanon, NH), and air-dried Kramer corn stover was provided by the National Renewable Energy Laboratory (NREL, Golden, CO, Lot #33A14). The relatively dry biomass (10-15% moisture) was knife milled to pass through a 1 mm particle size interior sieve using a laboratory mill (Model 4, Arthur H. Thomas Company, Philadelphia, PA). Biomass composition was determined according to the established National Renewable Energy Laboratory procedure (TP-510-42618, ver. 8-03-2012) in triplicates with a resulting composition of 40.9±0.3 wt. % glucan, 15.5±0.2% xylan, 2.1±0.1% mannan, 24.4±0.3% K-lignin, and 17.1% other material for maple wood and 32.7±0.4 wt. % glucan, 20.7±0.2% xylan, 2.6±0.1% arabinan, 16.0±0.1% K-lignin, and 28.0% other material for corn stover. Other materials needed for the biomass composition to total 100% were not characterized in this study but were expected to include minor saccharides, ash, sugar acids, acetate, and protein. Because arabinan, galactan, and mannan were not present in significant quantities and specific quantification of these minor sugars was difficult via HPLC, a decision was made to treat all quantified biomass pentosans as xylan and all hexosans as glucan.

The pure sugar reaction mixtures were prepared in 1:1 THF:water co-solvent solutions containing 20 g/L glucose or 10 g/L xylose and 0.1M (anhydrous) loading of the metal halide catalyst based on total liquid volume. Due to the different Brønsted acidities of each catalyst (Table 3), all solutions were normalized to 1.6 pH by titrating with 72 wt % concentrated sulfuric acid. An acidity of 1.6 pH was selected because it was close to the Brønsted acidity of the most acidic 0.1M $ZrOCl_2$-containing mixture (Table 3). Pure sugar solutions containing only sulfuric acid were also prepared and titrated to 1.6 pH to directly compare with metal halide acid catalysts as an acid control.

TABLE 3 pH of metal halide catalysts in co-solvent solution containing 1:1 THF: water[a]

| Catalyst | pH |
|---|---|
| $CrCl_3 \cdot H_2O$ | 3.13 |
| $AlCl_3 \cdot 6H_2O$ | 2.88 |
| $CuCl_2 \cdot 2H_2O$ | 2.78 |
| $FeCl_3 \cdot 6H_2O$ | 1.90 |
| $ZrOCl_2 \cdot 8H_2O$ | 1.65 |

[a]0.1 M catalyst loading based on each catalyst's anhydrous mass.

The reactions were carried out in non-stirred 14.3 mL Hastelloy pipe reactors (Hastelloy C-276, O.D. of 0.0127 m or 0.5 in.) with a wall thickness of 0.0008890 m (0.035 in.) and length of 0.1524 m (6 in.) to give a working reaction liquid volume of 10 mL. The pipe reactors were loaded into a heavy-duty custom steam chamber made of readily available steam rated (to 1 MPa steam pressure) 316 stainless steel 0.102 m (4 in.) internal diameter fittings (McMaster, Santa Fe Springs, CA). A high-pressure steam boiler (FB-075-L, Fulton Companies, Pulaski, NY) provided steam for rapid and stable heating of triplicate tube reactors. Temperature was monitored by both in-line pressure gauges and two K-type thermoprobes (Omega Engineering Co., Stamford, CT) and controlled by a PID controller via steam pressure. Due to the lengthwise construction of the tube reactors and the application of steam for heating and cold water for quenching, heat transfer was relatively rapid even for shorter reaction times (<10 min). Initial time was defined when a reaction temperature of 170° C. was reached. At the end of the reaction, the steam supply was shut off and the steam chamber was flooded with tap water to stop the reaction.

The liquid content of each reaction tube was transferred into 2 mL glass vials. These samples were centrifuged (2500 rpms for 20 min) and the supernatant was transferred into glass HPLC vials for HPLC analysis by an Agilent 1200 system equipped with a Bio-Rad Aminex® HPX-87H column and RI detector with an eluent (5 mM sulfuric acid) flow rate of 0.6 ml/min. The calculations for conversion of sugars and selectivity of secondary reactive intermediate products are shown below where $\Omega$ is the molar equivalence ratio from the starting sugar:

$$\% \text{ Conversion} = \left[1 - \frac{\text{Sugar concentration}_{final}(g/L)}{\text{Sugar concentration}_{initial}(g/L)}\right] * 100\% \quad (10)$$

$$\% \text{ Selectivity} = FP \text{ concentration}_{final}(g/L) * \Omega g/L \text{ Conversion} \quad (11)$$

$$\Omega_{furfural} = \frac{1.563}{\text{Concentration of xylose}_{initial}} \quad (12)$$

$$\Omega_{LA} = \frac{1.552}{\text{Concentration of glucose}_{initial}} \quad (13)$$

$$\Omega_{5-HMF} = \frac{1.428}{\text{Concentration of glucose}_{initial}} \quad (14)$$

Corn stover or maple wood solids loadings were calculated based on the total mass of the reaction (800 g) so that each reaction contained 5 wt % solids (40 g dry basis) and 1 wt % acid (7.6 g by anhydrous weight) based on THF:water mixture weight (760 g). Biomass mixtures were then allowed to pre-soak overnight at 4° C. to insure an even distribution of acid catalyst within the biomass pores. Contents were then left in the laboratory for an hour for the temperature to reach about room temperature prior to reaction.

The whole biomass slurry was then transferred to a high-pressure continuously stirred 1 L Parr reactor (Parr Instrument Company, Moline, IL) heated by a 4 kW fluidized sand bath (Model SBL-2D, Techne, Princeton, NJ). Mixing was performed by twin 6-blade impellers operating at 200 rpm by a top mounted electric motor, and the reactor temperature was directly measured by an in-line thermocouple (Omega, K-type). At the conclusion of a run, the reactor was cooled by quickly lowering it into a large room temperature water bath. All liquid containing receptacles were made of glass to prevent the loss of furfural and THF that was observed when plastics were used. The solids were then separated from the reaction liquor by vacuum filtration at room temperature through glass fiber filter paper (Fisher Scientific, Pittsburgh, PA). Mass and density of the liquid fraction were measured to complete accurate yield calculations. Due to the difference in density between the co-solvent mixtures and pure water, final densities were determined by weighing 25 mL of the reacted liquid in a volumetric flask after each reaction.

Liquid samples were analyzed by and Agilent 1200 HPLC system equipped with a Bio-Rad Aminex® HPX-87H column and RI detector with an eluent (5 mM sulfuric acid) flow rate of 0.6 ml/min. Since the HPX-87H column cannot distinguish between xylose, mannose, and galactose sugar peaks, the HPLC was also equipped with an Aminex® HPX-87P column to differentiate xylose from the other C6 sugars for yield calculations. Calculation of the reactive intermediate yields is given by Equation (15) where the molar equivalent number ($\theta$) of furfural (Eq. 16), LA (Eq. 17), and 5-HMF (Eq. 18) are individually calculated and divided by the fraction of the total glucan or xylan in the raw material.

$$\% \ FP \ \text{yield} = \theta_{FP} * \frac{FP_{final}(\text{g/L}) * \text{mass of liquor}_{final}(\text{g})}{\text{total biomass}_{initial}(\text{g}) * \text{density of liquor}_{final}(\text{g/L})} * 100\% \quad (15)$$

$$\theta_{furfural} = \frac{1.375}{\text{fraction of total xylan}_{initial}} \quad (16)$$

$$\theta_{LA} = \frac{1.396}{\text{fraction of total glucan}_{initial}} \quad (17)$$

$$\theta_{5-HMF} = \frac{1.286}{\text{fraction of total glucan}_{initial}} \quad (18)$$

Figure 13:
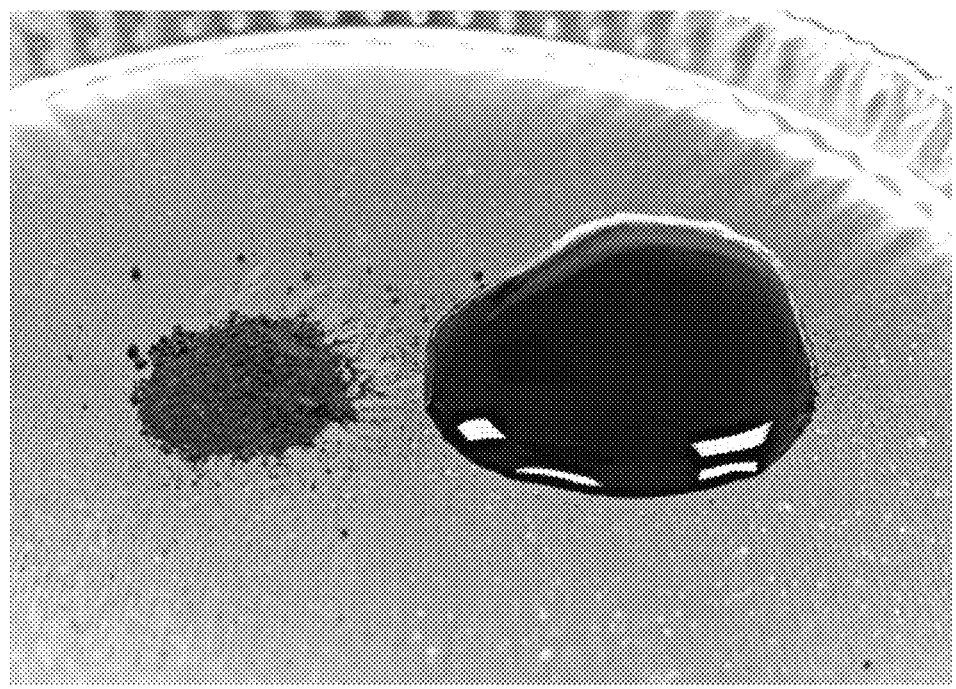
FIG. 13 shows an image: Left, precipitated lignin powder from maple wood after THF co-solvent with $FeCl_3$ catalyst. Right, same lignin powder shown dissolved in a large droplet of DMSO suitable for catalytic upgrading to fuels or chemicals.

For the recovery of extracted lignin, the reaction liquor was transferred to a glass bottle with a screw-on cap that was tapped with a 0.25 in. metal hose barb fitting. The fitting was connected by a flexible hose to a vacuum pump to perform vacuum distillation of THF. The liquor was agitated by a magnetic stir bar on a stir plate as THF was boiled off at room temperature under vacuum. Once the THF was removed from the aqueous liquor, the extracted lignin precipitates from solution as a black resinous solid. The solid lignin residue was then separated from the liquor and crushed to a fine powder by a ceramic mortar and pestle. The powder was then rinsed with water, air-dried, and then rinsed with diethyl ether. The resulting fine lignin powder product is shown in FIG. 13.

Table 3 shows the measured pH for the sugar co-solvent solutions containing 0.1M of each metal halide before reaction. It is known that metal oxide species form when the metal halides are hydrolyzed by water at elevated temperatures and the formation of OH ligands (as electron pair donors) during hydrolysis of the metal cations increases their acidity. The resulting pH of the solution is related to the first hydrolysis constant of the cationic species, where Zr and Fe cations to be the strongest. Metal chlorides are also known to form stable adducts with THF which can influence their ionizability and catalytic activity. As Brønsted acidity typically dominates sugar dehydration kinetics, the pH was normalized for all the sugar solutions to 1.6 using sulfuric acid (close to that of the most acidic metal halide) prior to each reaction. Doing so allowed a better understanding of how the relative Lewis strength of each catalyst influenced their selectivity to secondary reactive intermediates, the propensity for degradation of final products, and the tunability of the catalysts for optimizing co-production of furfural and 5-HMF from biomass.

Figure 10A:
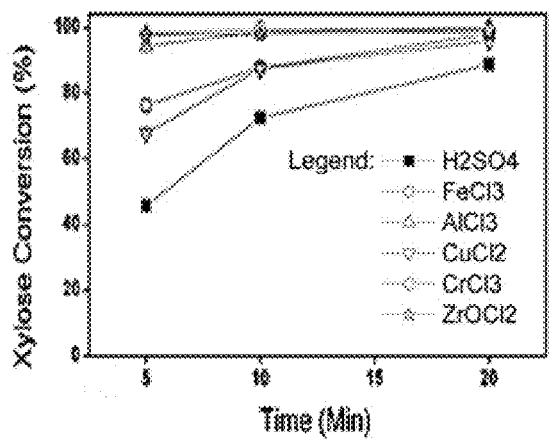
FIG. 10A-E shows conversions and selectivities for pure sugar reactions with metal halide acid catalysts in THF co-solvent mixture plotted against reaction time. (A) xylose and (B) glucose conversions and (C) furfural selectivity from xylose and (D) 5-HMF and (E) LA selectivity from glucose. Reaction conditions: 170° C., 20 g $L^{-1}$ glucose or 10 g $L^{-1}$ xylose, 1:1 THF:water ratio, 0.1M catalyst loading, and normalization of all solutions to pH 1.6 using 72% sulfuric acid. Black squares represent sulfuric acid control also titrated to 1.6 pH.
Figure 10B:
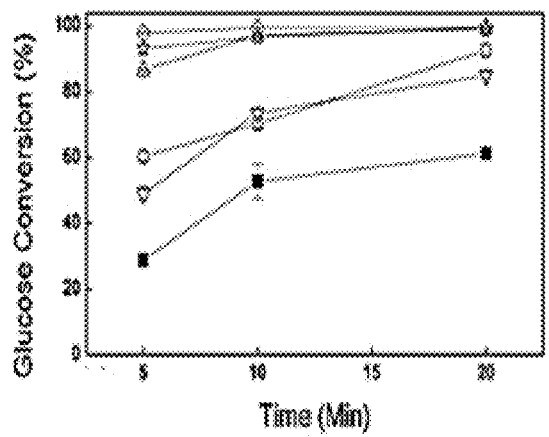

In order to characterize catalyst performance with this co-solvent system, pure glucose and xylose was reacted in 1:1 (v:v) THF:water solutions using different metal halides to compare sugar conversion and selectivity toward furfural, 5-HMF, and LA. Metal halides $AlCl_3 \cdot 6H_2O$, $CuCl_2 \cdot 2H_2O$, $CrCl_3 \cdot 6H_2O$, $FeCl_3 \cdot 6H_2O$, and $ZrOCl_2 \cdot 8H_2O$ were selected for this comparison. The sugar co-solvent solutions contained either 20 g $L^{-1}$ glucose or 10 g $L^{-1}$ xylose to simulate likely sugar concentrations from real biomass reactions at 5 wt % solids loading. Each metal halide was added based on their anhydrous catalyst mass to a concentration of 0.1M for each reaction. The sugar solutions were then loaded into Hastelloy tube reactors (10 mL working volume) and heated to 170° C. by a custom designed stainless steel steam chamber. The reaction proceeded until the steam was turned off and the chamber was flooded with cold tap water to quench the reaction. As shown in FIGS. 10A and 10B, the conversion of both xylose and glucose was significantly improved by all metal acid catalysts beyond what was possible for sulfuric acid alone in the THF co-solvent system. The relative performances of the metal halides were also very consistent for glucose and xylose. The most active metals were Cr, Zr, and Al due to their high Lewis acid strength, achieving nearly complete conversion of xylose by 5 min and glucose by 10 min. Cu- and Fe-based catalysts were notably slower in sugar conversion, but still achieved near complete conversion after 20 min.

Figure 14:
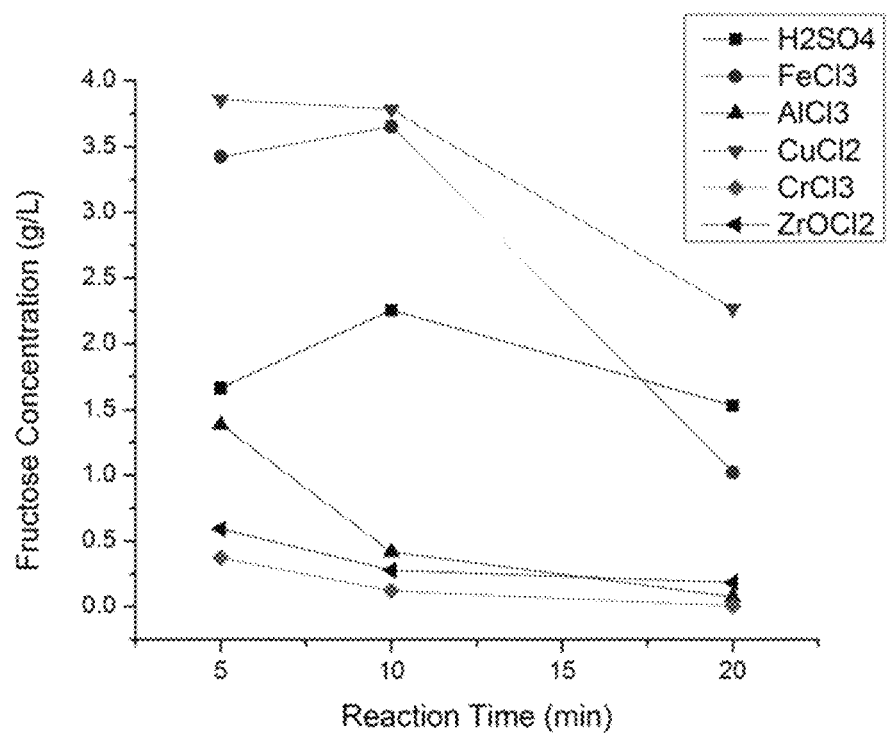
FIG. 14 shows liquid fructose concentration from pure glucose THF co-solvent reactions. Reaction conditions: 20 g $L^{-1}$ glucose, 1:1 THF:Water (vol), 170° C., 0.1M catalyst loading based on anhydrous mass.
Figure 15:
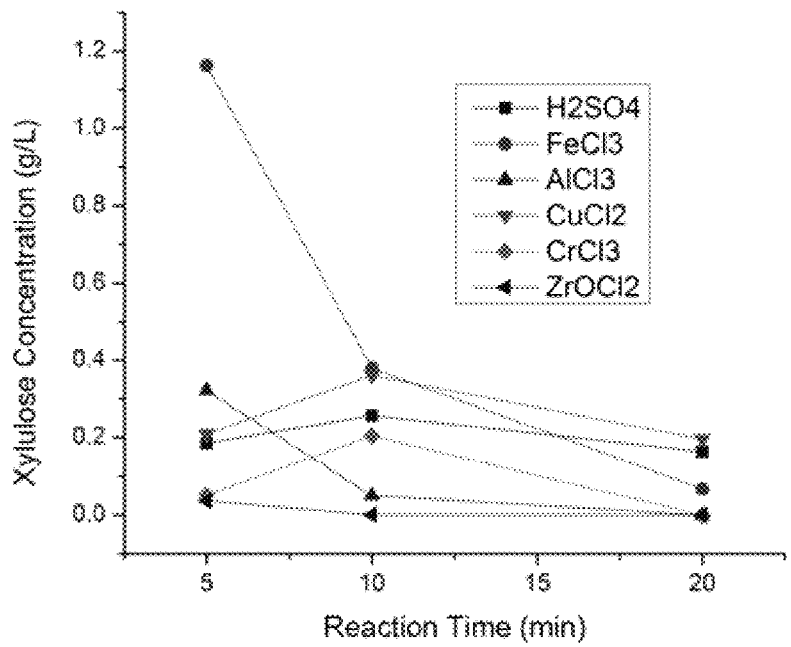
FIG. 15 shows liquid xylulose concentration from pure xylose THF co-solvent reactions. Reaction conditions: 10 g $L^{-1}$ xylose, 1:1 THF:Water (vol), 170° C., 0.1M catalyst loading based on anhydrous mass.

In all of the THF co-solvent sugar reactions, the accumulation of secondary sugar species whose retention times on the HPLC matched that of fructose and xylulose were observed. Their concentrations also tracked that of glucose and xylose disappearance over the course of the reaction suggesting that aldose-to-ketose isomerization occurred at a faster rate than sugar dehydration (Concentrations shown in FIGS. 14-15). This result agrees with what is known about metal halide-catalyzed sugar reactions: an open-chain dehydration mechanism is prevalent and ketose sugars dehydrate to furfural and 5-HMF more readily and faster than their aldose counterparts. Interestingly, ketose sugars were present in sulfuric acid reactions suggesting that THF can also interact with sugars to promote isomerization and supports early observations that THF co-solvent helped catalyze dehydration of aldose sugars over a comparable non-solvent reaction using only sulfuric acid. By promoting the more kinetically favorable open-chain dehydration pathway, THF may assist the metal halides to achieve high reactive intermediate yields.

Figure 10C:
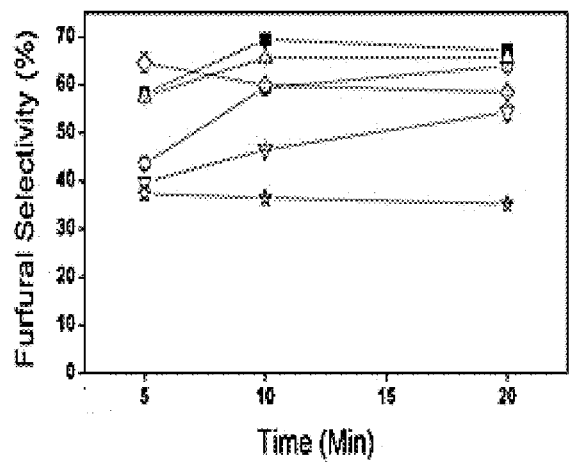

Selectivity to the secondary FPs was then calculated based on their concentrations after each reaction. In terms of furfural selectivity from xylose (FIG. 10C), sulfuric acid achieved a maximum of about 70% selectivity at 10 min that bested all other metal salt catalysts. This result suggested that although the Lewis acid character of the metal halides accelerated destruction of sugars, it also promoted competing loss reactions that diminished furfural accumulation in solution. These loss reactions can be attributed to condensation reactions between intermediate sugar species and furanic products to form humins. Due to rapid sugar conversion, the Cr catalyst achieved the highest furfural selectivity of about 65% earliest at 5 min, whereas $FeCl_3$ required 20 min to reach a maximum furfural selectivity of also about 65%. $ZrOCl_2$ had the lowest selectivity to furfural despite its ability to rapidly degrade xylose, likely due to the high formation of loss products.

Figure 10D:
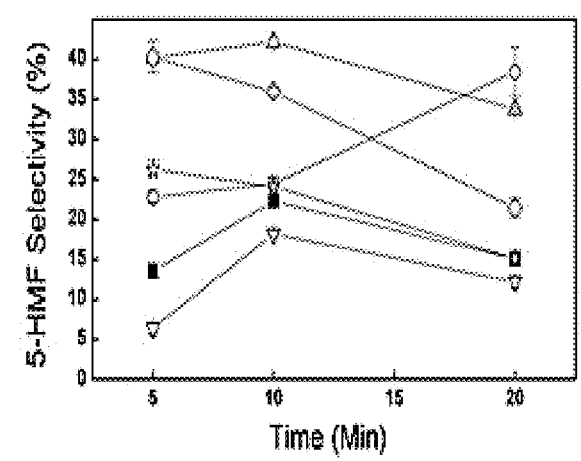

In the case of 5-HMF selectivity from glucose (FIG. 10D), all metal salts except $CuCl_2$ achieved higher selectivities (~40%) than sulfuric acid (~22%) in the co-solvent system, with Al, Cr, and Fe metals performing best. Again, the Fe-based catalyst required the longest reaction time and continually increased 5-HMF selectivity over the entire time, with it reaching 38% after 20 min. Interestingly, for all catalysts except $CuCl_2$, the highest selectivity for both furfural and 5-HMF occurred at approximately the same time with the best co-production of the furfurals demonstrated by Al, Cr, and Fe metals. Overall, however, 5-HMF selectivity was significantly lower than furfural selectivity owing to significant loss reactions to both condensation products and LA. This was apparent by the more drastic drop in 5-HMF selectivity than observed with furfural over the course of the reaction for all the metal halides except $FeCl_3$.

Figure 10E:
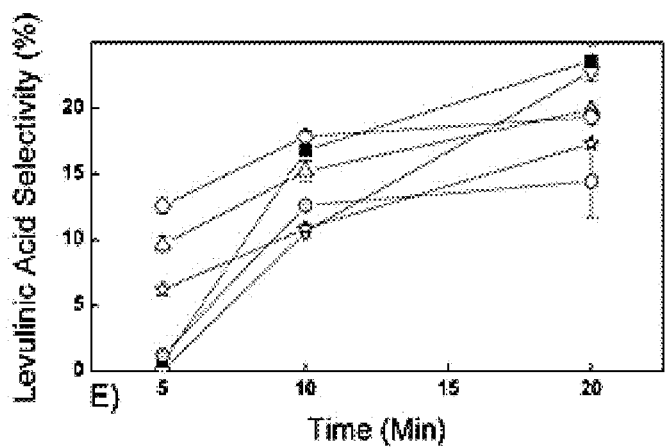

In the case of LA selectivity from glucose (FIG. 10E), all metal halides demonstrated lower selectivity to LA formation than sulfuric acid, in line with the goal of this study. As LA is produced from the hydrolysis of 5-HMF in this system, $CuCl_2$ and sulfuric acid achieved the highest LA selectivity as their selectivity towards 5-HMF was lowest. By extrapolation of the increasing trend of LA selectivity over longer reaction times, furfural and LA are likely not compatible co-products on a basis of their formation kinetics. Instead, furfural and 5-HMF can be produced together, whereas LA production would be most effectively targeted in a reaction independent of furfural. The more rapid sugar conversions observed with Cr-, Zr-, and Al-based halides compared to the slower Fe- and Cu-based halides are important differences among these catalysts that can help explain their performance in reacting actual biomass reported in the next section. Quantifiable parameters in the sugar reactions such as sugar conversion, reactive intermediate selectivity, and acidity of these metal halide catalysts will impact biomass conversion to achieve high combined furfural and 5-HMF yields.

The primary fractions of lignocellulosic biomass of interest for catalytic conversion to platform chemicals are cellulose, hemicellulose, and lignin. Xylan contained within amorphous hemicellulose presents the most readily available source of sugars as it can be completely hydrolyzed at mild to moderate severity reaction. Cellulose, on the other hand, is composed of crystalline polymeric glucose chains that are a primary source of C6 but remains the most recalcitrant sugar fraction to acid hydrolysis and is usually treated with cellulase enzymes after pretreatment to achieve high yields of glucose monomers in solution. Because the hemicellulose fraction of lignocellulosic biomass is far more acid-labile than crystalline cellulose, furfural is produced much sooner than 5-HMF and LA. Thus, an integrated conversion strategy to co-produce furfural and 5-HMF directly from biomass must be tunable to minimize competing side reactions of the least stable products to maximize product yields. For this reason, optimization for high furfural yields is a primary concern as the glucan remaining in the slower solubilizing cellulose fraction can be recovered as a solid product for further enzymatic and/or acid hydrolysis into glucose, biological conversion into alcohol fuels (e.g., ethanol) or thermochemical conversion into 5-HMF, and/or LA.

In addition to manipulation of the temperature, time, and acid loadings (combined reaction severity) to optimize yields from a biomass reaction, the THF co-solvent strategy allowed additional tuning by increasing THF concentrations in water to achieve greater selectivity to 5-HMF and increased biomass solubilization. The data compared the performance of the metal halide catalysts against sulfuric acid in 1 L THF co-solvent reactions with 5 wt % loading of maple wood or corn stover. Table 4 lists the reaction conditions at which the highest overall yields of furfural and 5-HMF were achieved from the biomass reactions. The THF:water ratio was also varied from 1:1 to 7:1 (by volume) to determine the extent of improved product yields and the limit of the single phase regime. The catalysts were loaded on a mass basis similar to commercial operation at a dilute 1 wt % in terms of the total liquid mass contained within the reaction.

TABLE 4

Acid-catalyzed co-production of furfural, 5-HMF, and LA from maple wood and corn stover in batch reactions with THF co-solvent[a]

| Run # | THF:Water[c] | Substrate[b] | Acid catalyst[d] | Time (min) | Solids remaining (%) | Furfural (%) | 5-HMF (%) | LA (%) |
|---|---|---|---|---|---|---|---|---|
| 1[e] | 1:1 | Maple wood | $H_2SO_4$ | 40 | 21 | 87 | 13 | 11 |
| 2 | 1:1 | Maple wood | $FeCl_3$ | 40 | 25 | 85 | 16 | 4.7 |
| 3 | 1:1 | Maple wood | $CuCl_2$ | 30 | 29 | 83 | 14 | 6.3 |
| 4 | 1:1 | Maple wood | $AlCl_3$ | 40 | 30 | 58 | 18 | 9.3 |

TABLE 4-continued

Acid-catalyzed co-production of furfural, 5-HMF, and LA from maple wood and corn stover in batch reactions with THF co-solvent[a]

| | | | | | | Yields (of theoretical) | | |
|---|---|---|---|---|---|---|---|---|
| Run # | THF:Water[c] | Substrate[b] | Acid catalyst[d] | Time (min) | Solids remaining (%) | Furfural (%) | 5-HMF (%) | LA (%) |
| 5 | 1:1 | Maple wood | $CrCl_3$ | 40 | 30 | 43 | 15 | 5.9 |
| 6 | 1:1 | Maple wood | $ZrOCl_2$ | 40 | 39 | 44 | 14 | 11 |
| 7 | 1:1 | Corn stover | $H_2SO_4$ | 40 | 19 | 84 | 16 | 11 |
| 8 | 1:1 | Corn stover | $FeCl_3$ | 40 | 31 | 85 | 12 | 4.0 |
| 9 | 1:1 | Corn stover | $ZrOCl_2$ | 40 | 43 | 38 | 14 | 12 |
| 10[e] | 3:1 | Maple wood | $H_2SO_4$ | 60 | 1 | 86 | 21 | 40 |
| 11 | 3:1 | Maple wood | $FeCl_3$ | 60 | 11 | 97 | 41 | 13 |
| 12 | 3:1 | Maple wood | $CuCl_2$ | 60 | 16 | 81 | 22 | 21 |
| 13 | 3:1 | Maple wood | $AlCl_3$ | 60 | 16 | 75 | 33 | 8.8 |
| 14 | 3:1 | Corn stover | $FeCl_3$ | 80 | 14 | 97 | 42 | 12 |
| 15 | 3:1 | Corn stover | $CuCl_2$ | 60 | 20 | 89 | 22 | 14 |
| 16 | 3:1 | Corn stover | $AlCl_3$ | 60 | 22 | 76 | 36 | 17 |
| 17 | 4:1 | Maple wood | $FeCl_3$ | 60 | 10 | 95 | 51 | 6 |
| 18 | 4:1 | Corn stover | $FeCl_3$ | 80 | 15 | 95 | 45 | 7 |
| 19 | 7:1 | Maple wood | $FeCl_3$ | 60 | 21 | 83 | 43 | 3 |

[a]All reactions were performed using a 1 L Parr reactor at 170 C. reaction temperature.
[b]5 wt % total solids loading.
[c]By volume ratio.
[d]All catalysts were loaded at 1 wt % anhydrous content.
[e]

As shown in Table 4 (Runs 1-9), with the exception of $CrCl_3$ and $ZrOCl_2$, metal halide catalysts demonstrated very consistent performance on both maple wood and corn stover, achieving maximum furfural yields close to that of sulfuric acid for a 1:1 THF:water mixture. 5-HMF yields were more comparable among catalysts, but metal halides produced lower LA yields compared to sulfuric acid owing to their increased selectivity to 5-HMF as found for pure sugar reactions. $FeCl_3$ was the best performer due to its higher Brønsted acidity, slower xylose conversion rates, and higher furfural selectivity at longer reaction times. $AlCl_3$ and $CuCl_2$ were middle performers owing to their more moderate Brønsted character, with trade-offs between high 5-HMF yields or high furfural yields, respectively, consistent with their selectivity with pure sugar reactions.

In order to investigate the extent of biomass solubilization for each catalyst, maple wood was reacted for 30 min in a 1:1 THF co-solvent mixture and 5 wt % initial biomass loading and 0.1M equivalent catalyst loading in the 1 L Parr reactor. FIG. 11 shows the composition of raw maple wood solids and the distribution of the major components into the solids remaining after reaction on the mass basis of 100 g of raw maple wood feed. As shown, biomass solubilization with metal halides was reduced compared to sulfuric acid. Also shown, over 90% of the maple wood K-lignin was removed during all metal halide reactions, except with $ZrOCl_2$, leaving behind a substantial amount of glucan-rich solids that contain no hemicellulose and minute amounts of other components. In the 1:1 THF reactions, maximizing solids recovery from the co-solvent reaction is crucial to enhance the economics of this process as the cleanly fractionated solids are suitable as a direct feed to produce fermentable glucose or used to make additional 5-HMF or LA. The non-sugar fraction may have resulted from accumulation of polymeric degradation products on the solids as the actual glucan remaining in the solids was much lower than from sulfuric acid catalyzed reactions.

Greater biomass solubilization at the higher solvent ratio of 3:1 (as shown in Table 4, runs 10-16) can support a reaction strategy that is more focused on furfural and 5-HMF production with less recoverable solids. At a 3:1 THF-to-water volume ratio, the top three performing (Al, Cu, Fe) metal halide catalysts greatly enhanced co-production of furfural and 5-HMF from maple wood and corn stover compared to sulfuric acid. In these reactions, $FeCl_3$ outperformed $CuCl_2$ and $AlCl_3$ in both furfural (97% yield for maple wood and corn stover) and 5-HMF (41% yield for maple wood and 42% for corn stover) production and biomass solubilization (11% solids remaining). $CuCl_2$ was unable to solubilize biomass as quickly as $FeCl_3$, and its lower 5-HMF yields from both maple wood and corn stover reactions could be explained by its lower 5-HMF selectivity (FIG. 10D) from glucose in the sugar reactions. For $AlCl_3$, tuning the reaction to achieve high furfural and 5-HMF co-production was difficult as the optimal reaction time for furfural was 20 min shorter than for 5-HMF. Thus, higher furfural yields were achieved with $CuCl_2$ at the expense of greater 5-HMF losses and higher 5-HMF yields were achieved with $AlCl_3$ at the expense of lower furfural yields. Overall, the consistency in performance between corn stover and maple wood in all reactions indicated that the THF co-solvent system may be largely feedstock agnostic and capable of achieving high yields in heterogeneous or mixed feedstock streams, appealing to commercial feasibility.

Figure 12:
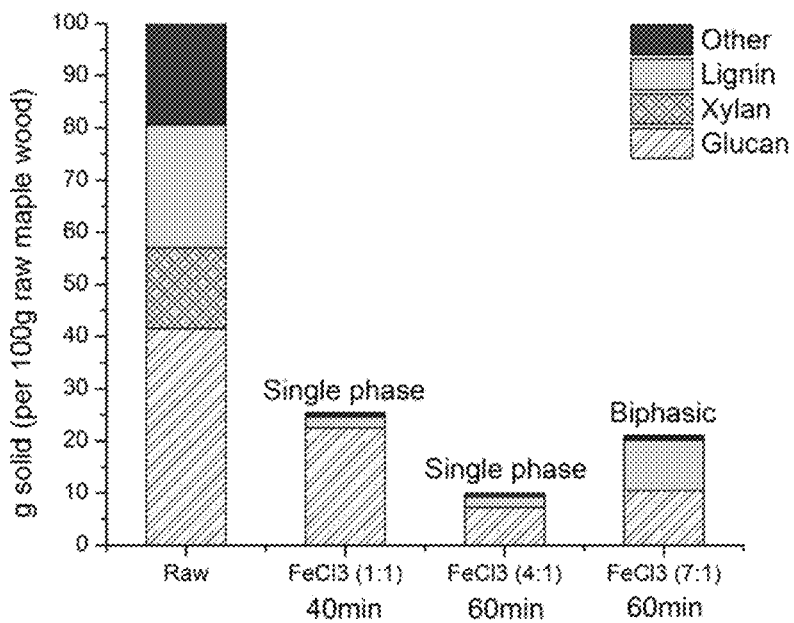
FIG. 12 shows composition of raw maple wood and distribution of major components to the solids remaining after reaction with THF co-solvent with $FeCl_3 \cdot 6H_2O$ at 1:1, 4:1, and 7:1 THF:water volume ratios. Solid mass is based on 100 g of initial maple wood fed to the systems. Suspected phase separation at 7:1 ratio is evident by larger lignin fraction, decreased solids solubilization, and increased remaining glucan fraction after 60 min reaction compared to the 4:1 ratio case. Reaction conditions: 5 wt % maple wood, 1 wt % $FeCl_3 \cdot 6H_2O$ based on anhydrous mass, 170° C.
Figure 16:
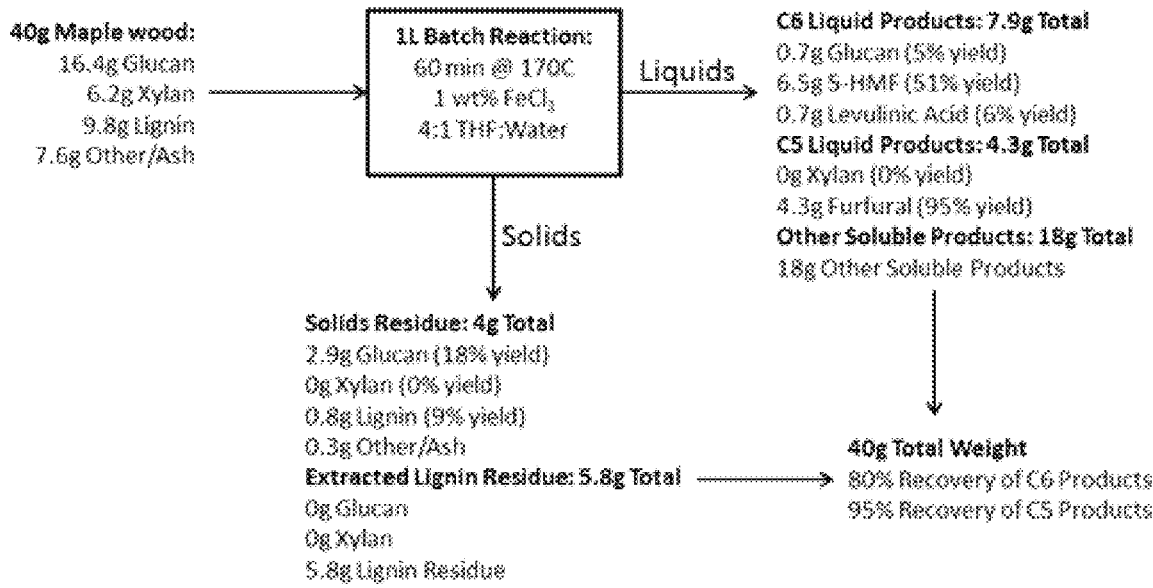
FIG. 16 shows and exemplary product flow and mass balance diagram describing the mass and yield of products recovered in both the solid and liquid portion after reaction. Data shown for reaction conditions listed in Table 3 Run 17 in the main article when the highest furfural and 5-HMF co-production yields were obtained. Total recovery of C6 and C5 products are calculated from the liquid and solid yields.

At a 4:1 solvent ratio (Table 4, run 17), $FeCl_3$ significantly outperformed sulfuric acid and the other metal halides and achieved the highest reported co-production yields of furfural (95% for maple wood and corn stover) and 5-HMF (51% for maple wood and 45% for corn stover) from lignocellulosic biomass by a one-pot single phase reaction. The higher solvent ratio was also beneficial to further reducing yields of LA (6-7% at 4:1 ratio), the most difficult product to recover due to its high boiling point. Thus, $FeCl_3$ proved to be the best metal halide for catalyzing co-production of furfural and 5-HMF in a biomass process using THF as a miscible co-solvent. Its strong acid strength allowed for reasonably fast deconstruction of both maple wood and corn stover, and the close reaction time for optimal furfural and 5-HMF production was beneficial to achieving good yields of both in one biomass reaction. As shown in FIG. 12, the 10% solids remaining after 4:1 co-solvent reaction of maple wood were very rich in glucan and could be recovered for efficient conversion to glucose by enzymes or further thermochemical reaction to 5-HMF and/or LA. A mass balance is shown for this run in FIG. 16 insuring accountability for 80% of the C6 products and 95% of the C5 products in the soluble and insoluble products after reaction.

The data show that at a 7:1 THF-to-solvent ratio (Table 4, run 19) or beyond, the behavior of the reaction suddenly shifted to resemble a two-phase regime. Although this was not qualitatively determine (such as by a sight glass in the reactor), the reaction kinetics and composition of the resulting solid material strongly suggested that the system was biphasic at such high THF ratios. In such a biphasic reaction, the dehydration kinetics of the aqueous phase are largely unaffected by the presence of the extracting solvent. Thus, THF would no longer be able to accelerate biomass solubilization as evident by the much higher solids fraction that remained after reaction (21% for Run 19 in Table 4). As shown in FIG. 12, compositional analysis of this solid fraction also revealed that a large glucan portion remained unsolubilized and most of the lignin was still intact and not extracted as would be expected in a single phase reaction with THF. Operating pressures of about 265 psig were also the highest observed and close to the sum of the saturated vapor pressures of water and THF, consistent with expectations for a two phase system. In addition, because biomass often has moisture contents of up to 50% by weight for woods, elevated solvent ratios would likely hurt biomass processing economics by consuming more heat that is an important consideration when comparing other co-solvent systems.

FIG. 2B outlines a proposed integrated THF co-solvent strategy for application of metal halide catalysts to enhance direct conversion of biomass into furfural and 5-HMF followed by two possibilities for their hydrogenation to MF and DMF, respectively. The experimental work in this study focused on producing high FP yields to be most compatible with leading downstream catalytic upgrading operations. In the process concept pictured in the figure, raw biomass and acid catalyst are loaded into a reactor along with THF co-solvent. Following reaction, high yields of both furfural and 5-HMF are achieved, and the reacted slurry is then collected and filtered to separate the solid residues. As THF is a low boiling solvent (66° C.) and forms a 95.4% azeotrope with water, it could be easily flashed off in a biorefinery to be recovered and recycled. In fact, room temperature vacuum distillation was sufficient to recover THF from the water phase.

The removal of THF also precipitates extracted biomass lignin as a solid that can be recovered and rinsed with diethyl ether to produce a very pure lignin powder as shown in the FIG. 13. This powder can in turn be re-dissolved in THF or DMSO and is suitable for catalytic upgrading to valuable chemicals. Afterwards, an appropriate organic solvent, such as MTHF, can be used as an immiscible solvent to extract and concentrate furfural and 5-HMF into the organic layer, leaving most of the trace sugars and contaminants in the aqueous layer. Alternatively, the aqueous stream resulting from THF removal could be fed directly to a catalytic reactor if desired, depending on the catalyst system chosen for upgrading furfural and 5-HMF. The aqueous stream containing the catalyst could be recycled as $FeCl_3$-containing aqueous streams have been shown to remain effective over several reactions in other systems.

Example 3

THF is an effective co-solvent for pretreatment of lignocellulosic biomass between solvent-to-water ratios of 1:5 (by volume) or higher, up to 7:1 (vol:vol) to specifically maximize monomeric sugar yields from biomass. Operating temperatures for THF co-solvent pretreatment range from 100° C. to 220° C. The range of acid catalyst loading needed for THF co-solvent pretreatment range of 0 wt % to 10 wt % depending on the type of acid. For this function, THF co-solvent pretreatments can be operated in batch, continuous flow-through, or plug flow configurations for either (A) traditional pretreatment of biomass followed by enzymatic hydrolysis or (B) direct solubilization of biomass to recover sugars without the need for an enzymatic hydrolysis step afterwards. In the latter case (B), THF co-solvent can be applied to a heated flow-through reactor at >1:1 THF:water ratios with little or no acid to effectively solubilize biomass and release mono- and oligo-saccharides that are then concentrated by the removal and recovery of THF. The total sugar yields (stage 1+stage 2) for typical pretreatments is calculated by the addition of total soluble sugar yield (C5+C6 sugars) released after the heated reaction (stage 1, pretreatment) and the total sugar soluble yield released after treatment of the pretreated solids with saccharification enzymes (stage 2).

Consecutive batch reactions at 170° C. were performed using dilute sulfuric acid (1 wt %, aka. dilute acid-only or no-THF). From the mass and composition of the remaining solids (per 100 g basis of raw maple wood) presented in FIG. 3E, a significantly higher degree of biomass solubilization was observed in the presence of THF than without. For the reactions containing a 1:1 mixture of THF and water, over 90 wt % of the acid-insoluble Klason lignin (K-lignin) initially present in maple wood was removed into the liquid phase by 10 min, producing a solid residue that was highly glucan-rich (>85 wt % glucan). In contrast, the composition of the remaining solids from reactions without THF show that K-lignin content was only slightly reduced at 30 min, but then quickly increased over time due to formation of pseudo-lignin and other acid-insoluble degradation products (FIG. 12). Also, the increased rate of glucan (cellulose) disappearance from the THF co-solvent pretreatments over the non-THF dilute acid-only case suggests that THF also catalyzes and promotes the hydrolysis of cellulose and likely hemicellulose as well.

Table 5 shows a comparison of the solubilization of hemicellulose, cellulose, and lignin fractions of poplar wood by pretreatment with dilute acid-only, organosolv, and THF co-solvent methods at the same reaction conditions. Because the reaction condition in these experiments were of lower severity than shown in FIG. 3, one can see that THF co-solvent pretreatment catalyzes and enhances the solubilization of all major lignocellulosic fractions beyond what is capable by an equivalent Organosolv (ethanol) or dilute acid-only pretreatment. This means that much lower severity reaction conditions are needed with THF co-solvent pretreatment to hydrolyze the same amount of sugars as the other two leading pretreatment methods.

TABLE 5

Solubilization of hemicellulose, cellulose, and lignin fractions of poplar by pretreatment with dilute acid-only, organosolv, and THF co-solvent methods

| Substrate | Solvent | Reaction time (min) | Temp (° C.) | Catalyst Loading | % Hemicellulose Solubilized | % Cellulose Solubilized | % Lignin Solubilized |
|---|---|---|---|---|---|---|---|
| Poplar wood | Water-only | 25 | 160 | 0.5 wt % $H_2SO_4$ | 85 | 2 | 0 |
| Poplar wood | 1:1 EtOH:Water | 25 | 160 | 0.5 wt % $H_2SO_4$ | 85 | 4 | 70 |
| Poplar wood | 1:1 THF:Water | 25 | 160 | 0.5 wt % $H_2SO_4$ | 91 | 15 | 86 |

FIG. 12 compares the composition of the remaining solids using different acid catalysts after THF co-solvent pretreatment with maple wood on a 100 g basis of the raw material. In FIG. 12, the reaction severities were significantly higher than typically used for pretreatment to recover sugars as the metal halide catalysts can be used to tune the pretreatment method to produce high yields of furfural from hydrolyzed C5 sugars instead. As shown, over 93% of the maple wood K-lignin was removed during all metal halide reactions, except with $ZrOCl_2$, and over 90% delignification with sulfuric acid in just 30 min reaction leaving behind a glucan-rich solid suitable for enzymatic hydrolysis to glucose or direct feed for fermentation processes such as simultaneous saccharification and fermentation (SSF) and consolidated bioprocessing (CBP). Tuning of the THF co-solvent with different catalysts is possible for co-production schemes from biomass such as co-producing xylose with glucose and furfural with glucose.

Figure 17:
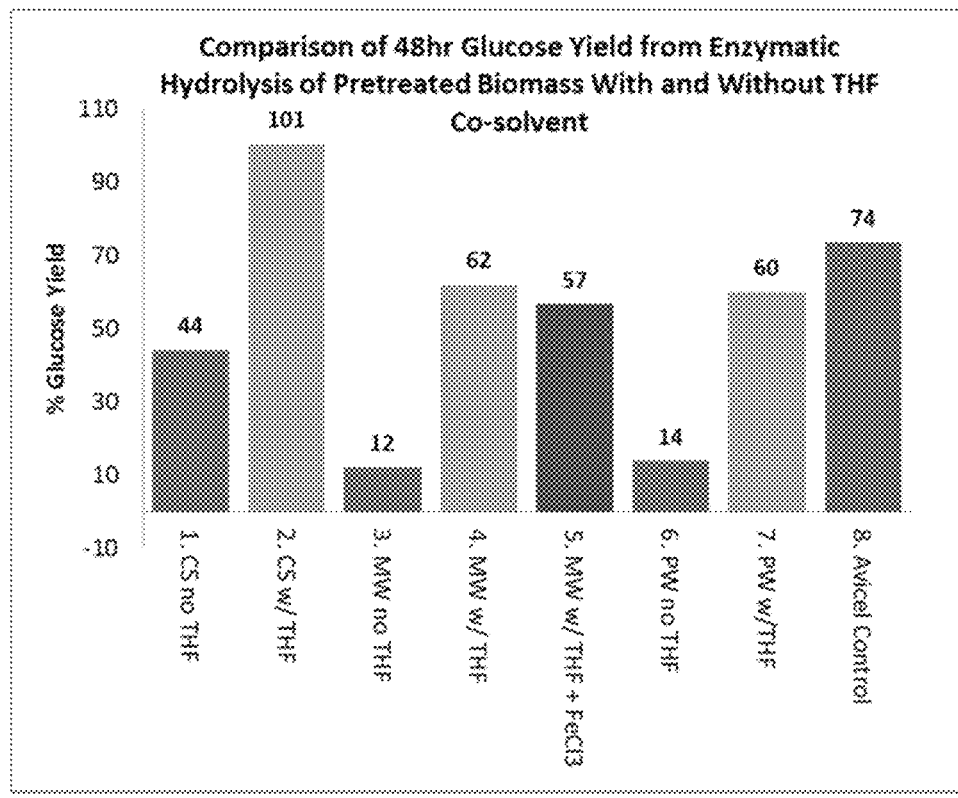
FIG. 17 shows a comparison between THF co-solvent pretreatment (col. 2, 4, 5, and 7) and non-THF dilute acid-only (DA) pretreatment (col. 1, 3, and 6) of 48 h glucose yield for enzymatic hydrolysis of corn stover (CS), maple wood (MW), and poplar wood (PW) at 50° C. in 50 mM citrate buffer (pH 5.0) at Accellerase® 1500 cellulase loading of 15 mg protein/g glucan in pretreated solids. Pretreatment reaction conditions: (1) 5 wt % corn stover, 170° C., water+1 wt % $H_2SO_4$, 40 min; (2) 5 wt % corn stover, 170° C., 1:1 THF:Water+1 wt % $H_2SO_4$, 40 min; (3) 5 wt % maple wood, 160° C., water+0.5 wt % $H_2SO_4$, 30 min; (4) 5 wt % maple wood, 160° C., 1:1 THF:Water+0.5 wt % $H_2SO_4$, 30 min; (5) 5 wt % maple wood, 170° C., 1:1 THF:Water+1 wt % (anhydrous weight) $FeCl_3 \cdot 6H_2O$, 30 min; (6) 5 wt % poplar wood, 160° C., water+0.5 wt % $H_2SO_4$, 30 min; (7) 5 wt % poplar wood, 160° C., 1:1 THF:Water+0.5 wt % $H_2SO_4$, 30 min; (8) Avicel® cellulose (97% pure alpha-cellulose).

As cellulase enzymes are the workhorses for hydrolyzing and converting glucan in biomass into fermentable glucose, the accessibility of the pretreated material to these enzymes indicate the effectiveness of the pretreatment strategy. The amount of cellulases used also contribute to a significant cost in the overall process so reducing the enzyme loadings necessary to achieve high sugar yields is beneficial. As shown in FIG. 17, acid catalyzed THF co-solvent pretreated material is much more accessible to enzymatic hydrolysis than reactions without THF at the same reaction conditions for multiple feedstocks corn stover, poplar wood, and maple wood. At only 48 h of enzymatic hydrolysis with moderate 15 mg protein/g glucan enzyme loading, the complete conversion of glucan to glucose is achieved from THF pretreated corn stover. Even for more recalcitrant biomass such as hardwoods, THF pretreated material was able to release 5× as much glucose than the non-THF case under the same conditions, achieving glucose yields similar to that of nearly pure Avicel® cellulose. Also shown in FIG. 17 (column 5), when THF co-solvent is used in conjunction with a metal halide catalyst at more severe reaction conditions suitable for furfural and 5-HMF production, the remaining glucan-rich material (shown in FIG. 12) is still highly digestible by enzymes for conversion into glucose.

Figure 18:
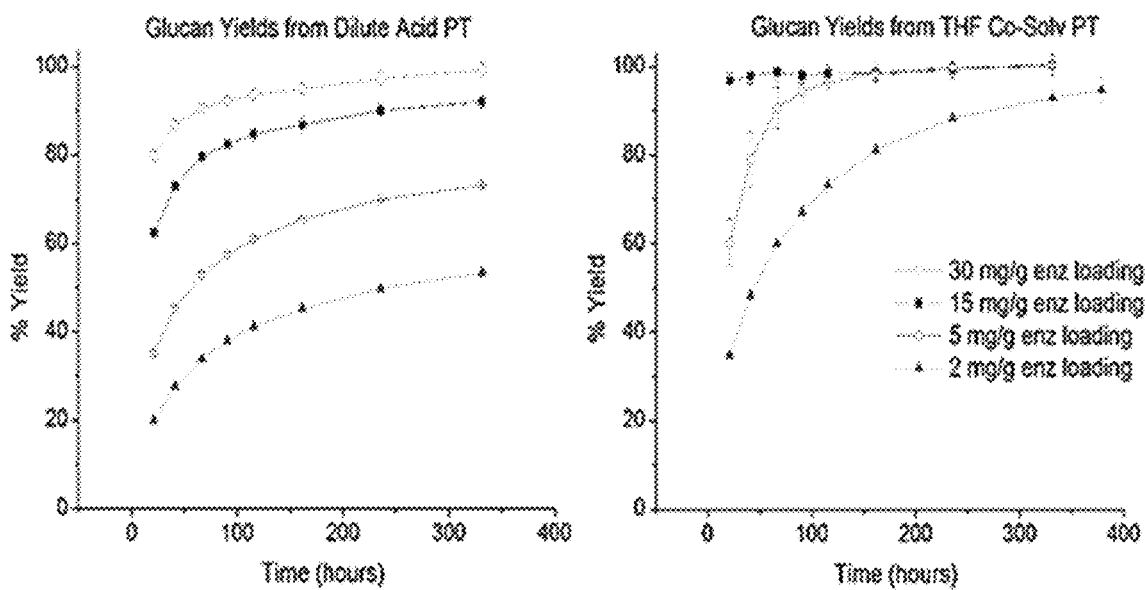
FIG. 18 shows a comparison of glucose released at various cellulase (Accellerase® 1500) enzyme loadings (mg enzyme protein/g glucan in pretreated sample) between THF co-solvent pretreatment and non-THF dilute acid-only (DA) pretreatment (PT) of corn stover using dilute sulfuric acid at their optimal total sugar release conditions. The X-axis represents enzymatic hydrolysis time in hours. Pretreatment conditions for dilute acid-only is 160° C. and 0.5% $H_2SO_4$ for 20 min (Optimum). Pretreatment conditions for THF is 1:1 THF:water, 150° C., 0.5% $H_2SO_4$, for 25 min (Optimum).
Figure 19:
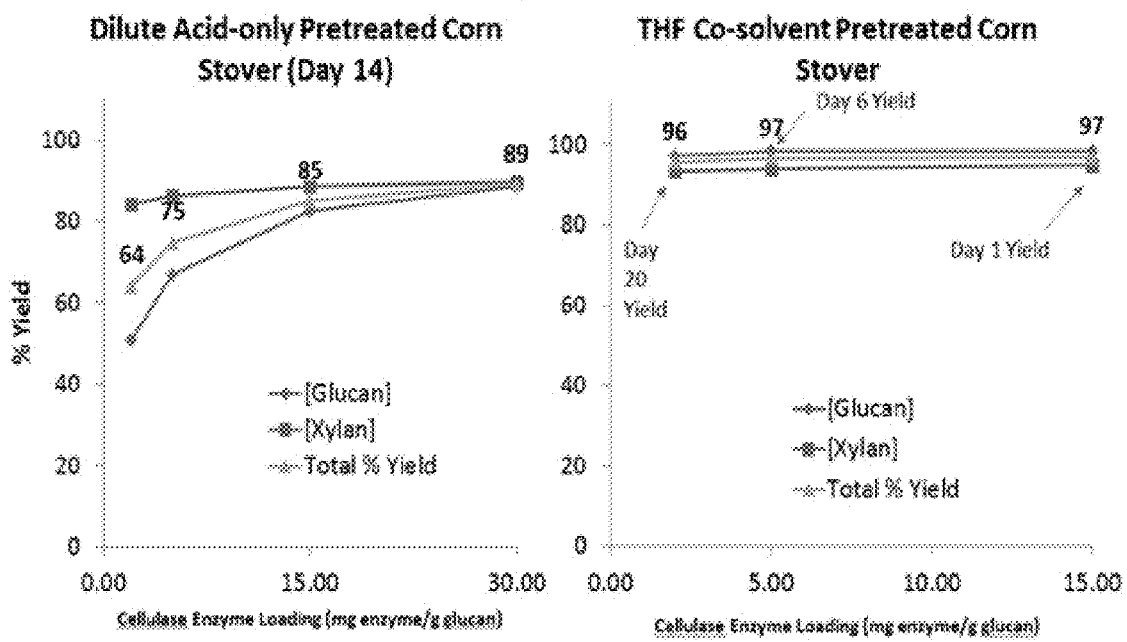
FIG. 19 shows a comparison of glucose, xylose, and glucose plus xylose yield achieved in Stage 1 and Stage 2 (Total % Yield) combined at various cellulase (Accellerase® 1500) enzyme loadings (mg enzyme protein/g glucan in pretreated sample) between THF co-solvent pretreatment (PT) and non-THF dilute acid-only (DA) pretreatment of corn stover using dilute sulfuric acid as an acid catalyst. The X-axis represents enzyme loading in mg protein/g glucan. Pretreatment conditions for dilute acid-only is 160° C. and 0.5% $H_2SO_4$ for 20 min (Optimum). Pretreatment conditions for THF is 1:1 THF:water, 150° C., 0.5% $H_2SO_4$, for 25 min (Optimum). The time in days is also indicated to show when the highest yields were achieved by enzymatic hydrolysis.

In FIGS. 18 and 19, both THF and non-THF pretreatments of corn stover were optimized for maximum total sugar recovery at 30 mg/g enzyme loading. The optimum conditions for THF co-solvent pretreatment (150° C., 25 min, 0.5 wt % acid) was found to be much less severe (lower energy requirement) than non-THF dilute acid-only pretreatment (160° C., 20 min, 0.5 wt % acid) at the same acid loadings. The enzyme loadings were then reduced in (see, FIG. 18) to observe how the glucose conversion yield responded. As shown in FIG. 18, THF co-solvent pretreated corn stover demonstrated significantly improved response to reduced loadings of Accellerase® 1500 cellulase (DuPont) than water-only pretreated corn stover when dilute sulfuric acid was used as a catalyst. In the case of THF co-solvent, at 5 and 15 mg/g glucan cellulase protein loadings, nearly all the glucan in the pretreated corn stover was released as glucose after 100 h. Also, by extrapolation of the glucose release curve for the 2 mg/g case, this low enzyme loading can also achieve nearly complete glucose release at longer hydrolysis times as shown in FIG. 18 (diamonds).

The total sugar yields (xylose and glucose) obtained from THF and non-THF pretreated corn stover is compared in FIG. 19. As shown, total sugar yield was effectively theoretical (~97%) at enzyme loadings as low as 2 mg/g glucan for THF pretreated corn stover (After 20 days), whereas dilute acid-only pretreated corn stover required 30 mg/g to achieve ~89% yield of total sugars (After 14 days). This means that THF co-solvent pretreatment effectively reduced the enzyme demand by <10× over traditional dilute acid-only pretreatment for corn stover. At only 15 mg/g glucan enzyme loading, THF co-solvent pretreated corn stover achieved maximum yields (97%) in only 1 day compared to dilute acid-only pretreatment's maximum yield (85%) achieved after 14 days. Not only is the maximum total sugar yield higher for THF co-solvent pretreatment, but the conversion by enzyme is much more rapid. This is indication that THF co-solvent is effective in maximizing accessibility by removal of hemicellulose and lignin fractions and doesn't inhibit enzyme function that is observed by dilute acid-only pretreatment. The high xylose yields observed also indicate that THF co-solvent is highly effective in maximizing sugar yields from both hemicellulose and cellulose biomass fractions.

Figure 20:
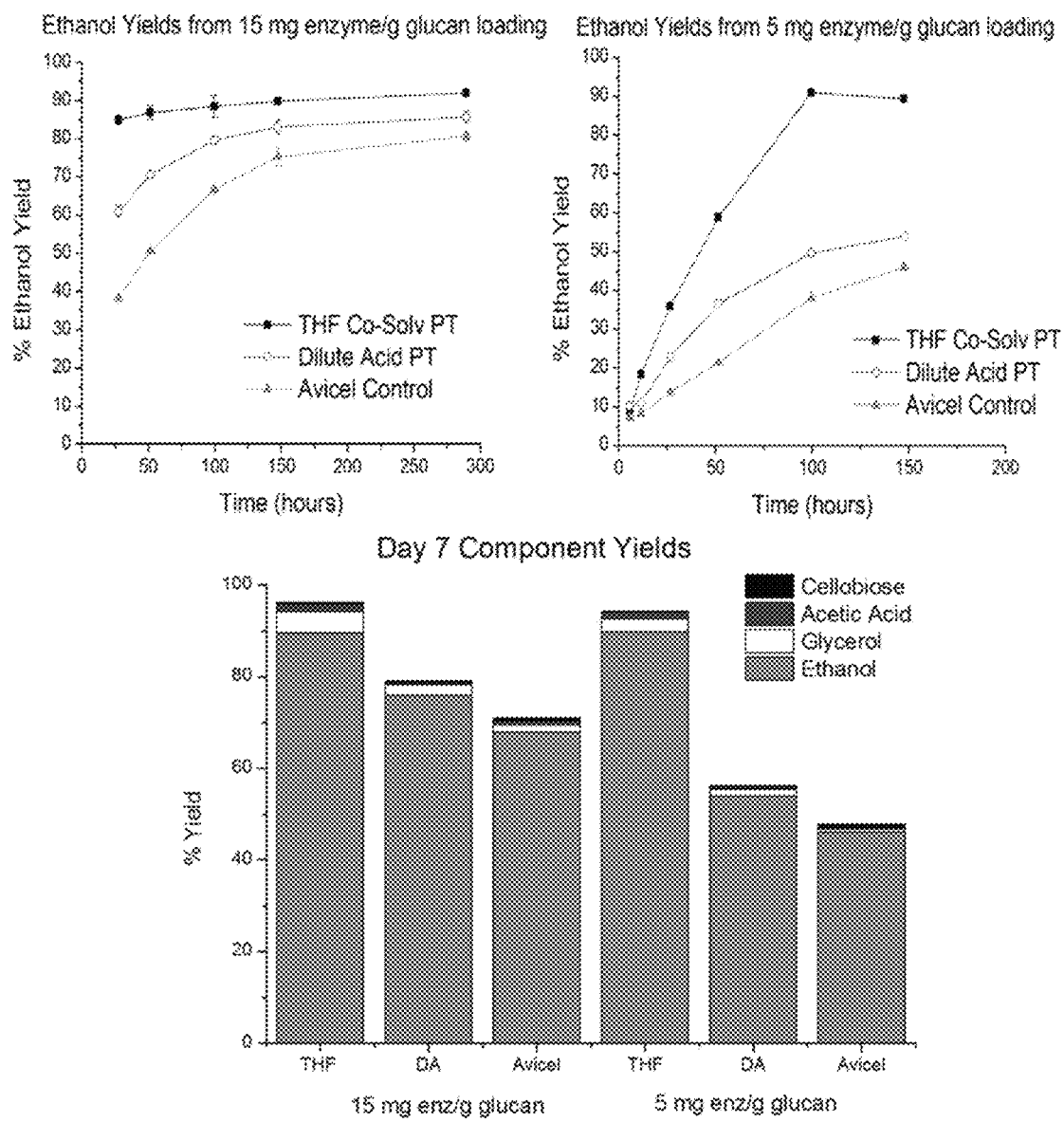
FIG. 20 shows a comparison of ethanol yields from simultaneous saccharification and fermentation (SSF) with *S. Cerevisiae* (strain D5A) using THF (top left) and non-THF dilute acid-only (DA, top right) pretreated corn stover and Avicel® cellulose. Comparison of broth component yields after 7 days fermentation is also shown in the bottom. Two enzyme protein loadings (5 mg/g glucan and 15 mg/g glucan) are shown. Pretreatment conditions for dilute acid-only is 160° C. and 0.5% $H_2SO_4$ for 20 min (Optimum). Pretreatment conditions for THF is 1:1 THF:water, 150° C., 0.5% $H_2SO_4$, for 25 min (Optimum). SSF conditions: prehydrolysis at 50° C. and 150 rpm for 18 h followed by fermentation at 37° C. and 130 RPM, 4 wt % glucan loading, inoculation of S. *Cerevisiae* (strain D5A) at 0.5 OD (optical density) at 600 nm in 250 mL shake flasks. X-axis represents fermentation time.

FIG. 20 compares the ethanol yields from SSF of THF and non-THF pretreated corn stover and Avicel® cellulose by *S. Cerevisiae* in 250 mL scale shake flask experiments (50 mL working volume). In these experiments, flasks were loaded with 4 wt % glucan, autoclaved for 30 minutes, pre-hydrolyzed with Accellerase 1500 cellulase at 15 mg/g glucan loading for 18 h (150 rpm, 50° C.), and inoculated to an optical density (OD) of 0.5 at 600 nm (130 RPM, 37° C.). As shown, THF co-solvent pretreated corn stover achieved higher ethanol yields at a sooner time in SSF than both dilute acid-only pretreated corn stover and Avicel® cellulose. With sufficient rinsing of the pretreated material by water (4 volume rinses through a vacuum filter), the THF pretreated material did not demonstrate any major inhibitory effects to ethanol titers. A maximum of 87% ethanol yield was achieved by THF pretreated corn stover, whereas only 80% ethanol yield was achieved by dilute acid-only pretreated corn stover, and 75% ethanol yield from Avicel® cellulose as a control.

Figure 21:
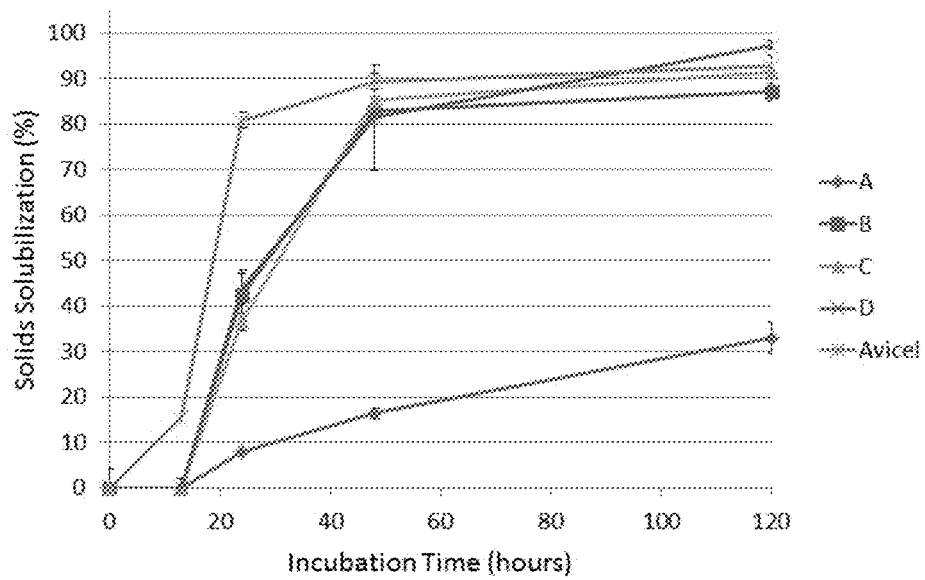
FIG. 21 shows a comparison of pretreated solids solubilization with *C. thermocellum* of THF co-solvent, ethanol-Organosolv, dilute acid-only (DA), and Avicel® cellulose in CBP fermentation experiments. Pretreatment conditions are listed in the table below the plot. CBP conditions: *C. thermocellum* DSM13131, 60° C. incubation at 5 g glucan/L solids loading in MTC media and 2% (v/v) inoculum size.

FIG. 21 compares the solids solubilization capability yields from CBP of pretreated poplar wood using *C. thermocellum* as the biological catalyst to perform both the saccharification of the sugars and simultaneous conversion of sugars to ethanol. In CBP, solids solubilization is a metric used to determine the performance of the substrate. The higher solids solubilization achieved by THF co-solvent pretreated poplar wood (FIG. 21; legend D) is comparable and better than that of ethanol-organosolv pretreatment (FIG. 21; legend B) and far superior to dilute acid-only pretreatment (FIG. 21; legend A). Reaction conditions and label identities are listed in the table below the plot in FIG. 21.

Other features and advantages of the disclosure will become more apparent from the following detailed description of the invention, when taken in conjunction with the accompanying exemplary drawings. Further modifications and improvements may additionally be made to the system and methods disclosed herein without departing from the scope of the disclosure. Accordingly, it is not intended that the invention be limited by the embodiments disclosed herein.

We claim:

1. A method for production of reactive intermediates from biomass, comprising:
    treating a biomass with a composition comprising an aqueous co-solvent mixture containing a co-solvent mixture of aqueous tetrahydrofuran (THF) at a ratio of THF:water of 1:3 to 2:1, and an acid catalyst between 0 and 1 weight % of the co-solvent mixture of aqueous tetrahydrofuran at a treatment temperature between 100° C. to 170° C. to produce a liquid phase comprising mono-saccharides, oligo-saccharides, furfural, and lignin;
    wherein the treatment of the biomass removes 70% or more of the lignin from the biomass,
    whereby a solid material is produced, which is greater than 85 weight % glucan; and
    whereby removing and/or recovering THF from the liquid phase produces a solid lignin product.

2. The method of claim 1, wherein the co-solvent mixture is monophasic at Standard Temperature and Pressure (STP) and monophasic at the treatment temperature, and the method further comprises:
    maintaining the co-solvent mixture for an operating time of 40 minutes or less; and
    utilizing the solid material produced in a subsequent process as a pulp, micro-crystalline cellulose, or glucose production by enzymatic hydrolysis.

3. The method of claim 2, whereby the co-solvent mixture of aqueous tetrahydrofuran prevents up to 7% less furfural loss from degradation as compared to a solution without THF.

4. The method of claim 2, whereby a furfural yield is greater than 60%.

5. The method of claim 2, whereby an operating time at the treatment temperature of less than or equal to 160° C. is for a time duration of less than 30 minutes and the co-solvent mixture of aqueous tetrahydrofuran (THF) is at the ratio of (THF:water) from 1:1 to 2:1.

6. The method of claim 2, further comprising:
    operating at the treatment temperature of less than 170° C. yields less than 60% furfural.

7. The method of claim 1, wherein the acid catalyst is a mineral acid.

8. The method of claim 7, wherein the acid catalyst is sulfuric acid.

9. The method of claim 1, further comprising: recapturing of the solid lignin product by THF.

10. The method of claim 1, further comprising removing and/or recovering furfural from a liquid phase after co-solvent treatment of the biomass by azeotropic distillation or solvent extraction.

11. The method of claim 1, wherein the solid material being greater than 85 weight % glucan is further treated with one or more enzymes that remove xylooligomers and higher chain length polymers of xylose to produce xylose monomers.

12. The method of claim 1, wherein the solid material being greater than 85 weight % glucan is further treated with one or more enzymes that remove glucooligomers and higher chain length polymers of glucose to produce glucose monomers.

13. The method of claim 1, wherein the solid material being greater than 85 weight % glucan is incubated with microorganisms and/or with added enzymes to produce an alcohol or other products by fermentation.

14. The method of claim 13, wherein the alcohol is ethanol.

15. The method of claim 13, wherein the alcohol contains 1 or more carbon molecules.

16. The method of claim 13, wherein the microorganism is selected from the group consisting of a yeast, a bacteria, a mold, and a fungi.

17. The method of claim 1, wherein the solid material being greater than 85 weight % glucan is used for producing paper pulp or dissolving pulp.

18. The method of claim 1, wherein the solid material being greater than 85 weight % glucan is hydrolyzed to glucose and glucose-oligomers using an acid selected from the group consisting of sulfuric acid, formic acid, acetic acid, trifluoroacetic acid and any combination thereof.

19. The method of claim 1, wherein the solid lignin product is at least 93% lignin.

20. The method of claim 1, wherein the solid lignin product is at least 90% lignin.

21. The method of claim 1, wherein the solid lignin product is at least 85% lignin.

22. A method for the combined solubilization and catalytic conversion of biomass to produce reactive intermediates from biomass, comprising:
    treating a biomass with a composition comprising an aqueous co-solvent mixture containing a co-solvent mixture of aqueous tetrahydrofuran (THF) at a ratio of (THF:water) from 1:1 to 2:1, and is between 0 and 1 weight % acid catalyst of the co-solvent mixture of aqueous tetrahydrofuran at a treatment temperature between 130° C. to 250° C. to produce a solid material and a liquid phase comprising furfural, 5-hydroxymethylfurfural, levulinic acid, and lignin; and
    removing and/or recovering THF from the liquid phase to produce a solid lignin product by removing greater than 70% of the lignin from the biomass, wherein
    (i) the co-solvent mixture is monophasic at Standard Temperature and Pressure and during treatment;
    (ii) the acid catalyst is added to achieve an adjusted pH that is less than or equal to 1.6; and (iii) the acid catalyst is selected from the group consisting of sulfuric acid, trifluoroacetic acid, FeCl$_3$, AlCl$_3$, CuCl$_2$ and any combination of sulfuric acid, trifluoroacetic acid, FeCl$_3$, AlCl$_3$, and CuCl$_2$.

23. The method of claim 22, wherein the furfural is further processed to be catalytically decarbonated or hydrogenated to produce a saturated or unsaturated furan.

24. The method of claim 22, wherein the solid lignin product is at least 93% lignin.

25. The method of claim 22, wherein the solid lignin product is at least 85% lignin.

26. The method of claim 22, further comprising one or more of:
   further comprising removing and/or recovering THF from the liquid phase after co-solvent treatment of the biomass;
   further comprising removing and/or recovery of lignin from the co-solvent treatment of the biomass by precipitation as a solid after the distillation of THF from the liquid phase;
   further comprising removing and/or recovering furfural and/or 5-HMF from a liquid phase of the co-solvent treatment of the biomass by distillation;
   further comprising removing and/or recovery furfural during and/or after co-solvent treatment by boiling and/or steam stripping, or
   further comprising extracting and/or recovering furfural and/or 5-HMF from a liquid phase of the co-solvent treatment of the biomass by a water-immiscible organic solvent.

27. The method of claim 22, whereby an operating time at the treatment temperature is less than 60 minutes.

28. The method of claim 22, whereby an operating time at the treatment temperature of between 150° C. and 220° C. is for a time duration of less than 40 minutes and whereby the co-solvent mixture of aqueous tetrahydrofuran (THF) is at the ratio of (THF:water) from 1:1 to 2:1.

29. The method of claim 22, whereby the solid material is greater than 80 weight % glucan.

30. A method for production of reactive intermediates from biomass, comprising:
   treating a biomass with a composition comprising a single phase co-solvent mixture of aqueous tetrahydrofuran (THF) and sulfuric acid as a catalyst under conditions to produce a liquid phase comprising biomass-derived, monomeric sugars, oligosaccharides, and lignin products and a solid material comprising biomass-derived polysaccharides;
   whereby a co-solvent mixture of aqueous tetrahydrofuran (THF) is at a ratio of (THF:water) from 1:1 to 2:1;
   wherein the sulfuric acid is less than or equal to 1.0 weight % of the co-solvent mixture at a treatment temperature at or below 170° C.;
   whereby the tetrahydrofuran has a primary role in limiting a furfural loss by resinification; and
   whereby a step of removing and/or recovery of lignin from the co-solvent treated biomass by precipitation as a solid after the removal of THF from the liquid phase.

* * * * *